(12) United States Patent
Bae et al.

(10) Patent No.: US 12,398,109 B2
(45) Date of Patent: Aug. 26, 2025

(54) 2-AMINO-2-(1,2,3-TRIAZOLE-4-YL) PROPANE-1,3-DIOL DERIVATIVE OF NOVEL COMPOUND FOR DIRECTLY INHIBITING ASM ACTIVITY, AND USE THEREOF

(71) Applicant: KYUNGPOOK NATIONAL UNIVERSITY INDUSTRY-ACADEMIC COOPERATION FOUNDATION, Daegu (KR)

(72) Inventors: Jae-Sung Bae, Daegu (KR); Hee Kyung Jin, Daegu (KR); Min Hee Park, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 946 days.

(21) Appl. No.: 17/048,672

(22) PCT Filed: Apr. 25, 2019

(86) PCT No.: PCT/KR2019/005019
§ 371 (c)(1),
(2) Date: Oct. 19, 2020

(87) PCT Pub. No.: WO2019/212196
PCT Pub. Date: Nov. 7, 2019

(65) Prior Publication Data
US 2021/0188784 A1    Jun. 24, 2021

(30) Foreign Application Priority Data

Apr. 30, 2018    (KR) .................... 10-2018-0050215

(51) Int. Cl.
C07D 249/04    (2006.01)
A23L 29/00    (2016.01)
A61P 25/28    (2006.01)

(52) U.S. Cl.
CPC .......... *C07D 249/04* (2013.01); *A23L 29/045* (2016.08); *A61P 25/28* (2018.01)

(58) Field of Classification Search
None
See application file for complete search history.

(56) References Cited

U.S. PATENT DOCUMENTS 9,724,334 B1    8/2017    Bae et al.
2017/0119912 A1    5/2017    Walji

FOREIGN PATENT DOCUMENTS

| EP | 3301090 A1 | 4/2018 |
| KR | 10-2017-0087813 A | 7/2017 |
| KR | 20170087813 A | 7/2017 |
| KR | 101811436 B1 | 12/2017 |
| KR | 1020180036318 A | 4/2018 |
| WO | 2010-017408 | 2/2010 |
| WO | 2010043000 A1 | 4/2010 |
| WO | 2018-199562 | 12/2017 |
| WO | 2018062638 A1 | 4/2018 |

OTHER PUBLICATIONS

Emre M. Isin, Charles S. Elmore, Göran N. Nilsson, Richard A. Thompson, and Lars Weidolf. Use of Radiolabeled Compounds in Drug Metabolism and Pharmacokinetic Studies. Chemical Research in Toxicology 2012 25 (3), 532-542 (Year: 2012).*
SciFinder. Substances of KR20170087813. Retrieved from the Internet on Sep. 19, 2023, https://scifinder-n.cas.org/search/substance/6509a2821e6bf717f4f1dbc6/1 (Year: 2023).*
Energy Education. The pH scale. Retrieved from the Internet on Oct. 26, 2023, https://energyeducation.ca/encyclopedia/The_pH_scale. (Year: 2023).*
International Search Report (English) and Written Opinion dated Jul. 22, 2019, from International Application No. PCT/KR2019/005019, 13 pages.
Supplementary European Search Report of EP 19796973, mailed Nov. 23, 2021, 1 page.
Written Opinion issued for Singaporean Application No. 11202010385R, dated Dec. 23, 2021.

* cited by examiner

*Primary Examiner* — James H Alstrum-Acevedo
*Assistant Examiner* — Lauren Wells
(74) *Attorney, Agent, or Firm* — Meunier Carlin & Curfman LLC

(57) ABSTRACT

The present invention relates to a composition for preventing or treating neurodegenerative diseases or depression, containing a 2-amino-2-(1,2,3-triazole-4-yl)propane-1,3-diol derivative as an active ingredient and more specifically, to a pharmaceutical composition for preventing or treating neurodegenerative diseases or depression, containing, as an active ingredient, the compound having an effect of directly inhibiting ASM activity.

10 Claims, 21 Drawing Sheets

Specification includes a Sequence Listing.

SCNPA 501
Chemical Formula : $C_{13}H_{22}N_4O_2$
Molecular Weight : 242.32

SCNPA 401
Chemical Formula : $C_{13}H_{24}N_4O_2$
Molecular Weight : 257.35

SCNPA 301
Chemical Formula : $C_{13}H_{26}N_4O_2$
Molecular Weight : 270.38

SCNPA 201
Chemical Formula : $C_{14}H_{28}N_4O_2$
Molecular Weight : 284.4

SCNPA 101
Chemical Formula : $C_{17}H_{34}N_4O_2$
Molecular Weight : 362.94

*p < 0.05
**p < 0.01
n = 6

*p < 0.05
**p < 0.01
n = 6

Biochemical IC$_{50}$

| Compound | SCNPA 501 | SCNPA 401 | SCNPA 301 | SCNPA 201 |
|---|---|---|---|---|
| ASM IC$_{50}$ (uM) | 1.86 | 1.82 | 1.75 | 1.14 |

| PK parameter (Plasma) | SCNPA 501 | | SCNPA 201 | | SCNPA 101 | |
|---|---|---|---|---|---|---|
| | p.o. 10 mg/kg | i.v. 1 mg/kg | p.o. 10 mg/kg | i.v. 1 mg/kg | p.o. 10 mg/kg | i.v. 1 mg/kg |
| $AUC_{last}$ (ng·h/mL) | 3128.46±2764.97 | 427.10±27.85 | 4156.27±356.61 | 850.97±80.60 | 2760.25±936.03 | 1423.06±207.38 |
| $AUC_{inf}$ (ng·h/mL) | 3130.75±2764.59 | 433.24±29.66 | 4286.30±250.86 | 852.16±81.13 | 2900.65±997.07 | 1477.10±197.74 |
| Half-life $_{plasma}$ (h) | 2.54±0.31 | 3.14±1.65 | 4.27±1.44 | 4.83±0.28 | 5.99±0.60 | 5.07±0.95 |
| MRT (h) | 4.2±2.05 | 2.54±0.80 | 6.09±1.46 | 3.84±0.5 | 7.06±0.84 | 5.47±0.30 |
| $C_{max}$ (ng/mL) | 554.74±91.95 | / | 748.18±225.27 | / | 438.81±115.96 | / |
| $C_0$ (ng/mL) | / | 631.89±106.79 | / | 365.40±293.42 | / | 525.02±158.25 |
| $T_{max}$ (h) | 0.50±0.43 | / | 0.63±0.31 | / | 0.58±0.38 | / |
| BA (%) | 72.26 | / | 50.33 | / | 19.64 | / |

AUC, Area under curve to last time point; MRT, Mean resident time; BA, Bioavailability n = 3

FIG. 6B

| PK parameter (Brain) | SCNPA 501 p.o.10 mg/kg | SCNPA 201 p.o.10 mg/kg | SCNPA 101 p.o.10 mg/kg |
|---|---|---|---|
| $AUC_{last}$ (ng·h/mL) | 4424.24±750.22 | 15124.37±2967.43 | 9961.12±1911.20 |
| $C_{max}$ (ng/mL) | 413.96±36.89 | 727.58±90.91 | 545.36±207.55 |
| Co (ng/mL) | / | / | / |
| $T_{max}$ (h) | 2.33±1.53 | 6.83±8.5 | 17.33±11.55 |
| MRT (h) | 3.83±0.12 | 11.80±1.38 | 14.50±2.14 |
| Brain distribution | 1.41 | 3.64 | 3.61 |

AUC, Area under curve to last time point; MRT, Mean resident time n = 3

| Compound | Microsome | % remaining after 0.5h | | half-life |
|---|---|---|---|---|
| | | mean | SD | (h) |
| SCNPA 501 | Human | 82.01 | 3.08 | 3.12 |
| | Mouse | 98.21 | 3.24 | 41.71 |
| SCNPA 201 | Human | 54.17 | 0.62 | 0.85 |
| | Mouse | 95.66 | 1.28 | 5.13 |
| SCNPA 101 | Human | 7.80 | 1.43 | 0.16 |
| | Mouse | 86.36 | 8.13 | 2.57 | n = 3

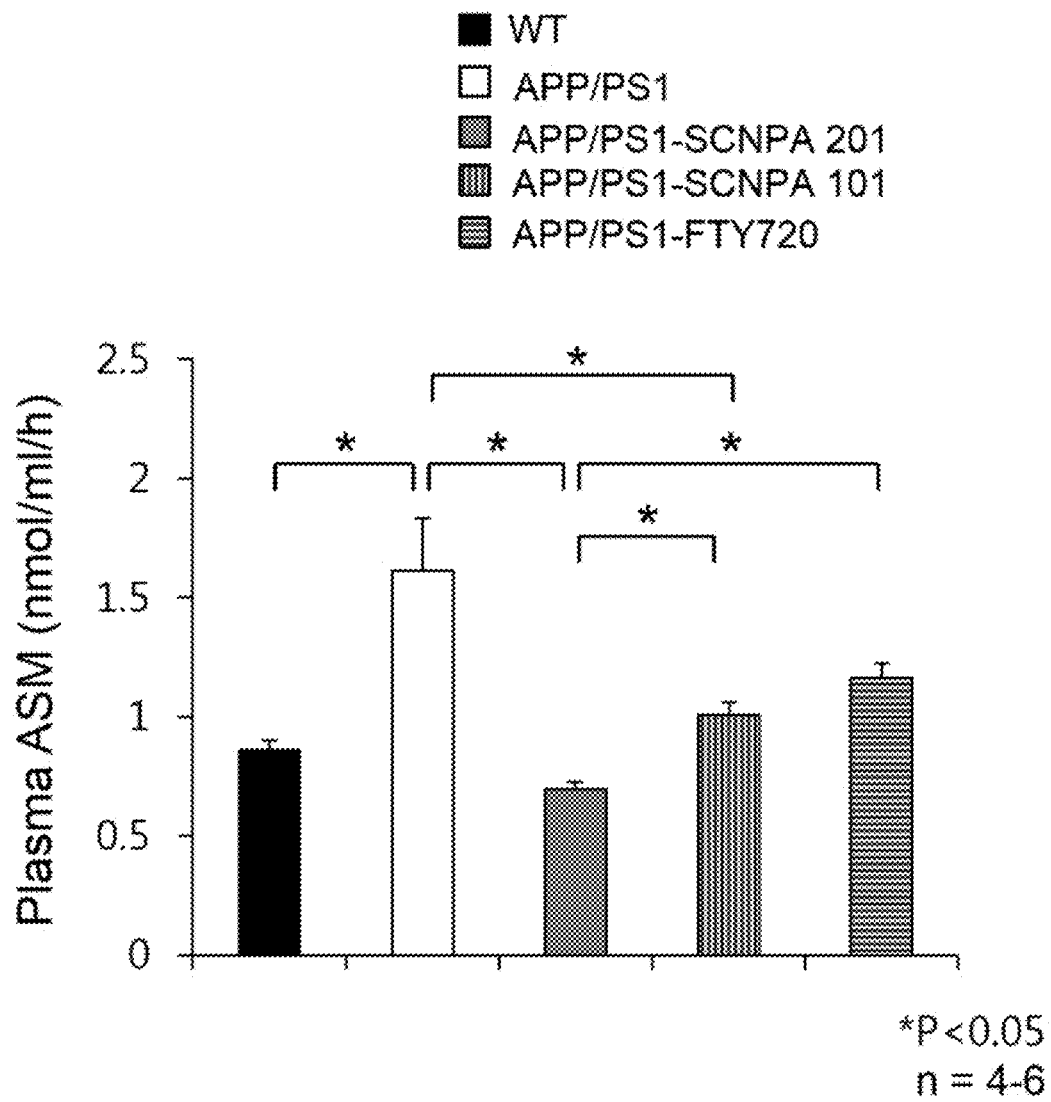

2-AMINO-2-(1,2,3-TRIAZOLE-4-YL) PROPANE-1,3-DIOL DERIVATIVE OF NOVEL COMPOUND FOR DIRECTLY INHIBITING ASM ACTIVITY, AND USE THEREOF

TECHNICAL FIELD

This application claims the priority of Korean Patent Application No. 10-2018-0050215, filed on Apr. 30, 2018, the entirety of which is a reference of the present application.

The present invention relates to a 2-amino-2-(1,2,3-triazol-4-yl)propane-1,3-diol derivative of a novel compound for directly inhibiting ASM activity and a use thereof, and more particularly, to a compound of Chemical Formula 1 and a use for preventing, improving or treating neurodegenerative diseases or depression thereof in the present specification.

REFERENCE TO A SEQUENCE LISTING

A Sequence Listing conforming to the rules of WIPO Standard ST.25 is hereby incorporated by reference. Said Sequence Listing has been filed as an electronic document via EFS-Web in ASCII formatted text. The electronic document, created on Mar. 1, 2021, is entitled "11239-006US1 2021_03_01 Replacement Sequence Listing.txt", and is 1,844 bytes in size.

BACKGROUND ART

Sphingolipid metabolism regulates normal cellular signaling, and abnormal changes in the sphingolipid metabolism affect various neurodegenerative diseases including Alzheimer's disease. Meanwhile, acid sphingomyelinase (ASM), which is an enzyme regulating sphingolipid metabolism, is a protein expressed in almost all types of cells, and plays an important role in sphingolipid metabolism and cell membrane turnover.

It has been reported that in the brain of patients with neurodegenerative diseases including Alzheimer's disease, the expression of ASM is significantly increased compared to that of normal people, and when inhibiting the expression of over-expressed ASM or inhibiting the activity of ASM, the accumulation of amyloid-β (Aβ) is inhibited and learning and memory are improved to exhibit a therapeutic effect of neurodegenerative diseases (Korean Patent Registration No. 10-1521117). In addition, recently, it is reported that the activity of ASM has been increased in neurological diseases such as depression, and the inhibition of ASM has an effect of alleviating depression (Nature medicine. 2013 Jul. 19(7): 934-938, PLoS One. 2016 Sep. 6; 11(9):e0162498). Therefore, the development of an ASM inhibitor, that is, a substance capable of inhibiting the expression or activity of ASM is promising as a useful treatment method for various diseases caused by an increase in ASM, including neurodegenerative diseases and depression.

Meanwhile, a direct ASM inhibitor has not been developed up to now, but several inhibitors capable of indirectly inhibiting ASM have been identified. First, tricyclic antidepressants (e.g. amitriptyline (AMI), desipramine, imipramine, etc.), which are most widely used as ASM indirect inhibitors, have been used in actual clinics as antidepressant drugs. Although not initially developed as an ASM inhibitor, it has been demonstrated by various study results that these drugs exhibit ASM inhibitory effects. A main mode of action of tricyclic antidepressants is an increase in the activity of neurotransmitters through inhibition of reuptake of the neurotransmitters in neurons, and exhibits an ASM inhibitory effect as a side effect. However, since the tricyclic antidepressants act on a nervous system and neurons to cause side effects such as hazy, an increase in light sensitivity, and vomiting, it is necessary to develop novel drugs capable of directly inhibiting the ASM activity.

DISCLOSURE

Technical Problem

Therefore, the present inventors have made efforts to develop a novel ASM inhibitor and found that a 2-amino-2-(1,2,3-triazol-4-yl)propane-1,3-diol derivative having a structure of Chemical Formula 1 was remarkable in an effect of directly inhibiting ASM activity to exhibit an excellent effect in the treatment of neurodegenerative diseases and depression, and completed the present invention.

Accordingly, an object of the present invention is to provide a compound of Chemical Formula 1 below or a salt thereof:

[Chemical Formula 1]

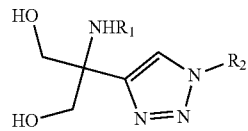

Wherein, $R_1$ is hydrogen; alkyl of 1 to 10 carbon atoms; or substituted or unsubstituted alkylcarbonyl of 1 to 5 carbon atoms, and $R_2$ is hydrogen; or alkyl of 1 to 10 carbon atoms, alkenyl of 2 to 10 carbon atoms, or alkynyl of 2 to 10 carbon atoms.

Another object of the present invention is to provide a pharmaceutical composition for preventing or treating neurodegenerative diseases or depression comprising the compound of Chemical Formula 1 above or a pharmaceutically acceptable salt thereof as an active ingredient.

Further, the present invention is to provide a pharmaceutical composition for preventing or treating neurodegenerative diseases or depression consisting of the compound of Chemical Formula 1 above or a pharmaceutically acceptable salt thereof as an active ingredient.

Further, the present invention is to provide a pharmaceutical composition for preventing or treating neurodegenerative diseases or depression essentially consisting of the compound of Chemical Formula 1 above or a pharmaceutically acceptable salt thereof as an active ingredient.

Yet another object of the present invention is to provide a food composition for improving neurodegenerative diseases or depression comprising the compound of Chemical Formula 1 above or a pharmaceutically acceptable salt thereof as an active ingredient.

Further, the present invention is to provide a food composition for improving neurodegenerative diseases or depression consisting of the compound of Chemical Formula 1 above or a pharmaceutically acceptable salt thereof as an active ingredient.

Further, the present invention is to provide a food composition for improving neurodegenerative diseases or depression essentially consisting of the compound of Chemical Formula 1 above or a pharmaceutically acceptable salt thereof as an active ingredient.

Still another object of the present invention is to provide a composition for diagnosing neurodegenerative diseases or depression comprising a compound of Chemical Formula 1 below to which a diagnostic agent or detection agent is bound or a pharmaceutically acceptable salt thereof as an active ingredient.

Further, the present invention is to provide a composition for diagnosing neurodegenerative diseases or depression consisting of a compound of Chemical Formula 1 below or a pharmaceutically acceptable salt thereof as an active ingredient.

Further, the present invention is to provide a composition for diagnosing neurodegenerative diseases or depression essentially consisting of a compound of Chemical Formula 1 below or a pharmaceutically acceptable salt thereof as an active ingredient.

[Chemical Formula 1]

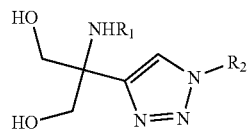

Wherein,
$R_1$ is hydrogen; alkyl of 1 to 10 carbon atoms; or substituted or unsubstituted alkylcarbonyl of 1 to 5 carbon atoms,
$R_2$ is hydrogen; or alkyl of 1 to 10 carbon atoms, alkenyl of 2 to 10 carbon atoms, or alkynyl of 2 to 10 carbon atoms, and
the defined alkyl, alkenyl, alkynyl or alkylcarbonyl each contains or does not contain radioactive isotopes.

Still yet another object of the present invention is to provide a use of a compound of Chemical Formula 1 below or a pharmaceutically acceptable salt thereof for preparing an agent for preventing or treating neurodegenerative diseases or depression.

[Chemical Formula 1]

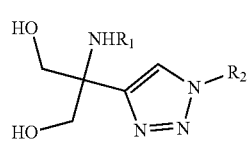

Wherein,
$R_1$ is hydrogen; alkyl of 1 to 10 carbon atoms; or substituted or unsubstituted alkylcarbonyl of 1 to 5 carbon atoms, and
$R_2$ is hydrogen; or alkyl of 1 to 10 carbon atoms, alkenyl of 2 to 10 carbon atoms, or alkynyl of 2 to 10 carbon atoms.

Still yet another object of the present invention is to provide a method for preventing or treating neurodegenerative diseases or depression characterizing administering an effective dose of a composition containing the compound of Chemical Formula 1 above or a pharmaceutically acceptable salt thereof as an active ingredient to a subject in need thereof.

Still yet another object of the present invention is to provide a use of a compound of Chemical Formula 1 below to which a diagnostic agent or detection agent is bound or a pharmaceutically acceptable salt thereof for preparing an agent for diagnosing neurodegenerative diseases or depression.

[Chemical Formula 1]

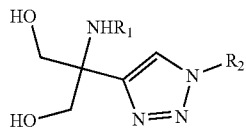

Wherein,
$R_1$ is hydrogen; alkyl of 1 to 10 carbon atoms; or substituted or unsubstituted alkylcarbonyl of 1 to 5 carbon atoms,
$R_2$ is hydrogen; or alkyl of 1 to 10 carbon atoms, alkenyl of 2 to 10 carbon atoms, or alkynyl of 2 to 10 carbon atoms, and
the defined alkyl, alkenyl, alkynyl or alkylcarbonyl each contains or does not contain radioactive isotopes.

Still yet another object of the present invention is to provide a method for diagnosing neurodegenerative diseases or depression comprising administering an effective dose of a composition containing the compound of Chemical Formula 1 above to which a diagnostic agent or detection agent is bound or a pharmaceutically acceptable salt thereof as an active ingredient to a subject suspected of neurodegenerative diseases or depression.

Technical Solution

In order to achieve the above objects, the present invention provides a compound of Chemical Formula 1 below or a salt thereof:

[Chemical Formula 1]

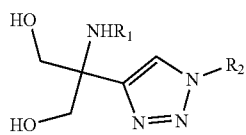

Wherein,
$R_1$ is hydrogen; alkyl of 1 to 10 carbon atoms; or substituted or unsubstituted alkylcarbonyl of 1 to 5 carbon atoms, and
$R_2$ is hydrogen; or alkyl of 1 to 10 carbon atoms, alkenyl of 2 to 10 carbon atoms, or alkynyl of 2 to 10 carbon atoms.

In order to achieve another object of the present invention, the present invention provides a pharmaceutical composition for preventing or treating neurodegenerative disease or depression comprising the compound of Chemical Formula 1 above or a pharmaceutically acceptable salt thereof as an active ingredient.

Further, the present invention provides a pharmaceutical composition for preventing or treating neurodegenerative diseases or depression consisting of the compound of Chemical Formula 1 above or a pharmaceutically acceptable salt thereof as an active ingredient.

Further, the present invention provides a pharmaceutical composition for preventing or treating neurodegenerative diseases or depression essentially consisting of the compound of Chemical Formula 1 above or a pharmaceutically acceptable salt thereof as an active ingredient.

In order to achieve yet another object of the present invention, the present invention provides a food composition for improving neurodegenerative diseases or depression comprising the compound of Chemical Formula 1 above or a pharmaceutically acceptable salt thereof as an active ingredient.

Further, the present invention provides a food composition for improving neurodegenerative diseases or depression consisting of the compound of Chemical Formula 1 above or a pharmaceutically acceptable salt thereof as an active ingredient.

Further, the present invention provides a food composition for improving neurodegenerative diseases or depression essentially consisting of the compound of Chemical Formula 1 above or a pharmaceutically acceptable salt thereof as an active ingredient.

In order to achieve still another object of the present invention, the present invention provides a composition for diagnosing neurodegenerative diseases or depression comprising a compound of Chemical Formula 1 below to which a diagnostic agent or detection agent is bound or a pharmaceutically acceptable salt thereof as an active ingredient.

Further, the present invention provides a composition for diagnosing neurodegenerative diseases or depression consisting of a compound of Chemical Formula 1 below to which a diagnostic agent or detection agent is bound or a pharmaceutically acceptable salt thereof as an active ingredient.

Further, the present invention provides a composition for diagnosing neurodegenerative diseases or depression essentially consisting of a compound of Chemical Formula 1 below to which a diagnostic agent or detection agent is bound or a pharmaceutically acceptable salt thereof as an active ingredient.

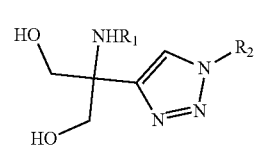

[Chemical Formula 1]

Wherein, $R_1$ is hydrogen; alkyl of 1 to 10 carbon atoms; or substituted or unsubstituted alkylcarbonyl of 1 to 5 carbon atoms, $R_2$ is hydrogen; or alkyl of 1 to 10 carbon atoms, alkenyl of 2 to 10 carbon atoms, or alkynyl of 2 to 10 carbon atoms, and the defined alkyl, alkenyl, alkynyl or alkylcarbonyl each contains or does not contain radioactive isotopes.

In order to achieve still yet another object of the present invention, the present invention provides a use of a compound of Chemical Formula 1 below or a pharmaceutically acceptable salt thereof for preparing an agent for preventing or treating neurodegenerative diseases or depression.

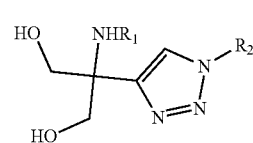

[Chemical Formula 1]

Wherein, $R_1$ is hydrogen; alkyl of 1 to 10 carbon atoms; or substituted or unsubstituted alkylcarbonyl of 1 to 5 carbon atoms, and $R_2$ is hydrogen; or alkyl of 1 to 10 carbon atoms, alkenyl of 2 to 10 carbon atoms, or alkynyl of 2 to 10 carbon atoms.

In order to achieve still yet another object of the present invention, the present invention provides a method for preventing or treating neurodegenerative diseases or depression characterizing administering an effective dose of a composition containing the compound of Chemical Formula 1 above or a pharmaceutically acceptable salt thereof as an active ingredient to a subject in need thereof.

In order to achieve still yet another object of the present invention, the present invention provides a use of a compound of Chemical Formula 1 below to which a diagnostic agent or detection agent is bound or a pharmaceutically acceptable salt thereof for preparing an agent for preventing or treating neurodegenerative diseases or depression:

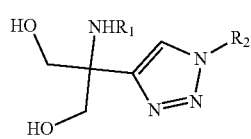

[Chemical Formula 1]

Wherein, $R_1$ is hydrogen; alkyl of 1 to 10 carbon atoms; or substituted or unsubstituted alkylcarbonyl of 1 to 5 carbon atoms, $R_2$ is hydrogen; or alkyl of 1 to 10 carbon atoms, alkenyl of 2 to 10 carbon atoms, or alkynyl of 2 to 10 carbon atoms, and the defined alkyl, alkenyl, alkynyl or alkylcarbonyl each contains or does not contain radioactive isotopes.

In order to achieve still yet another object of the present invention, the present invention provides a method for diagnosing neurodegenerative diseases or depression comprising administering an effective dose of a composition containing the compound of Chemical Formula 1 above to which a diagnostic agent or detection agent is bound or a pharmaceutically acceptable salt thereof to a subject suspected of neurodegenerative diseases or depression.

Hereinafter, the present invention will be described in more detail.

The present invention provides a compound of Chemical Formula 1 below or a salt thereof:

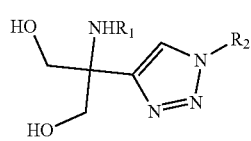

[Chemical Formula 1]

Wherein, $R_1$ is hydrogen; alkyl of 1 to 10 carbon atoms; or substituted or unsubstituted alkylcarbonyl of 1 to 5 carbon atoms, and $R_2$ is hydrogen; or alkyl of 1 to 10 carbon atoms, alkenyl of 2 to 10 carbon atoms, or alkynyl of 2 to 10 carbon atoms.

In the present invention, the "alkyl" refers to a linear or branched hydrocarbon of 1 to 10 carbon atoms. Representative examples of the alkyl include methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl, but are not limited thereto.

The term "carbonyl" used in the present invention refers to a —C(O)— group.

In the present invention, the "alkylcarbonyl" refers to the alkyl group bound to a parent molecular residue by the carbonyl group as defined above. Representative examples of the alkylcarbonyl include acetyl, 1-oxopropyl, 2,2-dimethyl-1-oxopropyl, 1-oxobutyl and 1-oxopentyl, but are not limited thereto.

In the present invention, when the alkylcarbonyl is "substituted" alkylcarbonyl, the alkylcarbonyl may be substituted with one or more substituents selected from the group consisting of hydroxy, halogen, cyano, nitro and amino.

In the present invention, the "alkenyl" refers to a linear or branched hydrocarbon of 2 to 10 carbon atoms containing at least one carbon-carbon double bond formed by the removal of two hydrogens. Representative examples of the alkenyl include ethenyl, 2-propenyl, 2-methyl-2-propenyl, 3-butenyl, 4-pentenyl, 5-hexenyl, 2-heptenyl, 2-methyl-1-heptenyl, and 3-decenyl, but are not limited thereto.

In the present invention, the "alkynyl" refers to a linear or branched hydrocarbon group of 2 to 10 carbon atoms including one or more carbon-carbon triple bonds. Representative examples of the alkynyl include acetylenyl, 1-propynyl, 2-propynyl, 3-butynyl, 2-pentynyl, and 1-butynyl, but are not limited thereto.

Preferably, in the present invention, the $R_1$ may be hydrogen or acetyl, and the $R_2$ may be alkyl of 1 to 10 carbon atoms. More preferably, in the present invention, the $R_1$ may be hydrogen, and the $R_2$ may be alkyl of 4 to 10 carbon atoms. Much more preferably, in the present invention, the $R_1$ may be hydrogen, and the $R_2$ may be alkyl of 6 to 9 carbon atoms. Most preferably, in the present invention, the $R_1$ may be hydrogen, and the $R_2$ may be alkyl of 9 carbon atoms.

Further, the present invention provides a pharmaceutical composition for preventing or treating neurodegenerative diseases or depression comprising a compound of Chemical Formula 1 below or a pharmaceutically acceptable salt thereof as an active ingredient.

Further, the present invention provides a pharmaceutical composition for preventing or treating neurodegenerative diseases or depression consisting of a compound of Chemical Formula 1 below or a pharmaceutically acceptable salt thereof as an active ingredient.

Further, the present invention provides a pharmaceutical composition for preventing or treating neurodegenerative diseases or depression essentially consisting of a compound of Chemical Formula 1 below or a pharmaceutically acceptable salt thereof as an active ingredient.

[Chemical Formula 1]

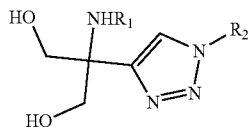

Wherein,
$R_1$ is hydrogen; alkyl of 1 to 10 carbon atoms; or substituted or unsubstituted alkylcarbonyl of 1 to 5 carbon atoms, and $R_2$ is hydrogen; or alkyl of 1 to 10 carbon atoms, alkenyl of 2 to 10 carbon atoms, or alkynyl of 2 to 10 carbon atoms.

It has been reported that in the brain of patients with neurodegenerative diseases including Alzheimer's disease, the expression of ASM is significantly increased compared to that of normal people, and when inhibiting the expression of over-expressed ASM or inhibiting the activity of ASM, the accumulation of amyloid-β (Aβ) is inhibited and learning and memory are improved to exhibit a therapeutic effect of neurodegenerative diseases (Korean Patent Registration No. 101521117). In addition, recently, it has been reported that the activity of ASM has been increased in neurological diseases such as depression, and the inhibition of ASM has an effect of alleviating depression (Nature medicine. 2013 Jul. 19(7):934-938, PLoS One. 2016 Sep. 6; 11(9): e0162498). Therefore, a substance capable of inhibiting the expression or activity of ASM may be developed as a useful therapeutic agent for diseases including neurodegenerative diseases and depression.

According to an embodiment of the present invention, it was confirmed that the compound of Chemical Formula 1 above has a very excellent effect of inhibiting the activity of ASM and has effects of reducing Aβ plaques in an Alzheimer's brain environment, alleviating neuroinflammation, etc., and thus may be used as an agent for preventing or treating neurodegenerative diseases including Alzheimer's disease or depression.

According to another embodiment of the present invention, it was confirmed that the compound of Chemical Formula 1 above may directly inhibit the activity of ASM by binding to an ASM active site in fibroblasts of Alzheimer's patients. On the other hand, it was confirmed that the compound of Chemical Formula 1 above did not exhibit an effect of inhibiting sphingosine-1-phosphate (S1P) and sphingosine-1-phosphate receptor 1 (S1PR1), but was a direct inhibitor capable of specifically inhibiting ASM.

In the compound of Chemical Formula 1 above included in the pharmaceutical composition of the present invention, the $R_1$ is preferably hydrogen or acetyl, and the $R_2$ may be alkyl of 1 to 10 carbon atoms. More preferably, in the present invention, the $R_1$ may be hydrogen, and the $R_2$ may be alkyl of 4 to 10 carbon atoms. Most preferably, in the present invention, the $R_1$ may be hydrogen, and the $R_2$ may be alkyl of 6 to 9 carbon atoms.

According to an embodiment of the present invention, it was confirmed that when the $R_2$ in Chemical Formula 1 above is alkyl of more than 10 carbon atoms, compared to alkyl of 10 or less carbon atoms, not only the brain distribution of the compound is sharply lowered, but also the metabolism caused by human liver microsomes is rapidly increased. In developing a therapeutic agent for brain diseases such as neurodegenerative diseases, considering that it is very important that a drug shows a high distribution in a brain region by passing through a blood-brain barrier and that metabolic stability in the liver is a very important factor that can influence the distribution of an oral administrated drug in the body because the drug needs to be subjected to a first pass effect when administered orally, it is not preferable that the $R_2$ in Chemical Formula 1 above has more than 10 carbon atoms.

According to another embodiment of the present invention, it was confirmed that when the $R_2$ in Chemical Formula 1 above is alkyl of more than 10 carbon atoms, as compared with alkyl of 10 or less carbon atoms, an effect of inhibiting ASM activity, an effect of reducing Aβ plaque deposition in the brain, an effect of improving memory, anxiety, and depression in an Alzheimer's animal model, and an effect of reducing neuroinflammation in the brain are reduced. Therefore, in terms of pharmacological activity, it is not preferable that the $R_2$ in Chemical Formula 1 above has more than 10 carbon atoms.

The present invention includes not only the compound represented by Chemical Formula 1 above, but also a pharmaceutically acceptable salt thereof, and solvates, hydrates, racemates, or stereoisomers that may be prepared therefrom.

As the pharmaceutically acceptable salt of the compound represented by Chemical Formula 1 of the present invention, an acid addition salt formed by a pharmaceutically acceptable free acid is useful. The acid addition salt is obtained from inorganic acids such as hydrochloric acid, nitric acid, phosphoric acid, sulfuric acid, hydrobromic acid, hydroiodic acid, nitrous acid, phosphorous acid, etc., non-toxic organic acids such as aliphatic mono and dicarboxylates, phenyl-substituted alkanoates, hydroxy alkanoates and alkandioates, aromatic acids, aliphatic and aromatic sulfonic acids, etc., and organic acids such as acetic acid, benzoic acid, citric acid, lactic acid, maleic acid, gluconic acid, methanesulfonic acid, 4-toluenesulfonic acid, tartaric acid, fumaric acid, etc. Types of these pharmaceutically non-toxic salts may include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxy benzoate, methoxybenzoate, phthalate, terephthalate, benzene sulfonate, toluene sulfonate, chlorobenzene sulfonate, xylene sulfonate, phenyl acetate, phenyl propionate, phenyl butyrate, citrate, lactate, β-hydroxybutyrate, glycolate, malate, tartrate, methane sulfonate, propane sulfonate, naphthalene-1-sulfonate, naphthalene-2-sulfonate, mandelate, etc.

The acid addition salt according to the present invention may be prepared by a conventional method, for example, by dissolving the compound represented by Chemical Formula 1 above in an excessive amount of acid aqueous solution and precipitating the salt by using a water-miscible organic solvent, for example, methanol, ethanol, acetone or acetonitrile. In addition, the mixture may be dried by evaporating a solvent or an excess of acid, or the precipitated salt is suction-filtered to prepare the acid addition salt.

In addition, a pharmaceutically acceptable metal salt may be prepared by using a base. An alkali metal salt or an alkaline earth metal salt may be obtained, for example, by dissolving the compound in an excessive amount of alkali metal hydroxide or alkaline earth metal hydroxide solution, filtering a non-dissolved compound salt, and then evaporating and drying a filtrate. At this time, the metal salt is pharmaceutically suitable to prepare a sodium, potassium or calcium salt. Further, a silver salt corresponding thereto may be obtained by reacting the alkali metal or alkaline earth metal salt with an appropriate silver salt (e.g., silver nitrate).

In the present invention, a type of neurodegenerative disease is not particularly limited as long as the neurodegenerative disease is a neurological disease in which metabolic abnormality in sphingolipid or/and an increase in activity or expression of ASM acts as the cause of a disease in the art. The neurodegenerative disease may be selected from the group consisting of, for example, Alzheimer's disease, Parkinson's disease, progressive supranuclear palsy, multiple system atrophy, olivopontocerebellar atrophy (OPCA), Shire-Dragger syndrome, striatum-nigral degeneration, Huntington's disease, amyotrophic lateral sclerosis (ALS), essential tremor, corticobasal degeneration, diffuse Lewy body disease, Parkin's-ALS-dementia complex, pick disease, cerebral ischemia, and cerebral infarction, but is not limited thereto.

In the present invention, depression, that is, depressive disorder refers to a disease that causes a variety of cognitive, mental, and physical symptoms with decreased motivation and depression as main symptoms, resulting in a decrease in daily function. A detailed type of the depression of the present invention is not particularly limited as long as the depression is known as a depressive disorder in the art. For example, the depression includes major depressive disorder (MDD), vascular dementia depression, bipolar disorder, unipolar disorder, seasonal affective disorder (SAD), light depression, dysthymia, depression associated with neurodegenerative disease, or the like. Preferably, the depression may be depression due to an abnormal increase in ASM activity (overactivity).

The pharmaceutical composition according to the present invention may contain the compound of Chemical Formula 1 above or a pharmaceutically acceptable salt thereof alone or may be formulated in a suitable form with a pharmaceutically acceptable carrier, and further contain an excipient or a diluent. The 'pharmaceutically acceptable' generally refers to a non-toxic composition which does not cause an allergic reaction such as gastrointestinal disorder and dizziness or a similar reaction thereto when being physiologically acceptable and administered to the human.

The pharmaceutically acceptable carrier may further include, for example, a carrier for oral administration or a carrier for parenteral administration. The carrier for oral administration may include lactose, starch, cellulose derivatives, magnesium stearate, stearic acid, etc. In addition, the carrier for oral administration may include various drug delivery substances to be used for oral administration to peptide preparations. In addition, the carrier for parenteral administration may include water, suitable oil, saline, aqueous glucose, glycol, etc., and may further include a stabilizer and a preservative. The suitable stabilizer includes antioxidants such as sodium hydrogen sulfite, sodium sulfite or ascorbic acid. The suitable preservative includes benzalkonium chloride, methyl- or propyl-paraben, and chlorobutanol. The pharmaceutical composition of the present invention may further include a lubricant, a wetting agent, a sweetening agent, a flavoring agent, an emulsifying agent, a suspending agent, and the like in addition to the above ingredients. Other pharmaceutically acceptable carriers and preparations may be referred to as those known in the art.

The composition of the present invention may be administered to mammals including humans even by any method. For example, the composition may be administered orally or parenterally. The parenteral administration method is not limited thereto, but may be intravenous, intramuscular, intraarterial, intramedullary, intrathecal, intracardiac, transdermal, subcutaneous, intraperitoneal, intranasal, intestinal, local, sublingual or rectal administration.

According to an embodiment of the present invention, it was conformed that the compound of Chemical Formula 1 above of the present invention has not only excellent bioavailability, but also metabolic stability by human liver microsomes, which is dramatically improved compared to a previously reported ASM inhibitor. Therefore, preferably, the pharmaceutical composition of the present invention may be a pharmaceutical composition for oral administration.

The pharmaceutical composition of the present invention may be formulated as a preparation for oral administration or parenteral administration according to an administration route as described above. In the case of the preparation for oral administration, the composition of the present invention may be formulated as powders, granules, tablets, pills, sugarcoated pills, capsules, liquids, gels, syrups, slurries, suspensions, etc. by using methods known in the art. For example, the preparation for oral administration may be obtained as tablets or sugarcoated pills by mixing an active ingredient with a solid excipient, grinding the mixture, and then adding a suitable adjuvant to be processed as a granular mixture. Suitable examples of the excipient may include fillers, such as sugars including lactose, dextrose, sucrose, sorbitol, mannitol, xylitol, erythritol, maltitol, etc., starches including corn starch, wheat starch, rice starch, potato starch, etc., celluloses including cellulose, methyl cellulose, sodium carboxymethylcellulose, hydroxypropylmethyl-cellulose, etc., gelatin, and polyvinylpyrrolidone. In addition, in some cases, cross-linked polyvinylpyrrolidone, agar, alginic acid, sodium alginate, or the like may be added as a disintegrant. In addition, the pharmaceutical composition of the present invention may further include an anti-coagulating agent, a lubricant, a wetting agent, a fragrance, an emulsifier, and a preservative.

The preparation for parenteral administration may be formulated by methods known in the art in the form of injections, creams, lotions, external ointments, oils, moisturizers, gels, aerosols and nasal inhalants. These formulations are generally known to all pharmaceutical chemistries.

The total effective dose of the composition of the present invention may be administered to patients in a single dose, or may be administered in a multiple dose for a long period of time by a fractionated treatment protocol. In the pharmaceutical composition of the present invention, the contents of the active ingredients may vary depending on the degree of disease. Preferably, a preferred total dose of the pharmaceutical composition of the present invention may be about 0.01 μg to 10,000 mg, most preferably 0.1 μg to 100 mg per 1 kg of patient's body weight per day. However, the effective dose of the pharmaceutical composition to the patients is determined by considering various factors, such as the age, body weight, health conditions, and gender of a patient, the severity of disease, diet, and excretion rate, as well as a formulation method, an administration route and the number of treatment times. Accordingly, considering such an aspect, those skilled in the art may determine a suitable effective dose of the composition of the present invention. The pharmaceutical composition according to the present invention is not particularly limited to the formulations, the administration routes, and the administration methods as long as the effects of the present invention are shown.

Further, the present invention provides a food composition for improving neurodegenerative diseases or depression comprising a compound of Chemical Formula 1 below or a pharmaceutically acceptable salt thereof as an active ingredient.

Further, the present invention provides a food composition for improving neurodegenerative diseases or depression consisting of a compound of Chemical Formula 1 below or a pharmaceutically acceptable salt thereof as an active ingredient.

Further, the present invention provides a food composition for improving neurodegenerative diseases or depression essentially consisting of a compound of Chemical Formula 1 below or a pharmaceutically acceptable salt thereof as an active ingredient.

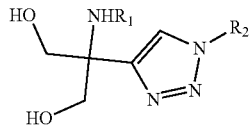

[Chemical Formula 1]

Wherein, $R_1$ is hydrogen; alkyl of 1 to 10 carbon atoms; or substituted or unsubstituted alkylcarbonyl of 1 to 5 carbon atoms, and $R_2$ is hydrogen; or alkyl of 1 to 10 carbon atoms, alkenyl of 2 to 10 carbon atoms, or alkynyl of 2 to 10 carbon atoms.

The food composition according to the present invention includes all types of functional foods, nutritional supplements, health foods, and food additives. These types may be prepared in various forms according to general methods known in the art.

For example, as the health foods, the food composition itself of the present invention may be prepared and drunk in the form of tea, juice, and drink or granulated, encapsulated, and powdered to be taken. In addition, the food composition of the present invention may be mixed with substances or active ingredients known to have an effect for prevention, improvement, or treatment of neurodegenerative diseases or depression to be prepared in the form of a composition.

Further, the functional foods may be prepared by adding the food composition of the present invention to beverages (including alcoholic beverages), fruits and processed foods thereof (e.g., canned fruits, bottled fruits, jams, marmalade, etc.), fish, meat and processed foods thereof (e.g., ham, sausage corn beef, etc.), breads and noodles (e.g., udon, buckwheat noodles, ramen, spaghetti, macaroni, etc.), juice, various drinks, cookies, syrup, dairy products (e.g., butter, cheese, etc.), edible plant oils, margarine, vegetable proteins, retort foods, frozen foods, various seasonings (e.g., soybean paste, soy sauce, sauces, etc.), etc.

The preferred content of the food composition according to the present invention is not limited thereto, but is preferably 0.01 to 50 wt % of the total weight of the finally produced food. In order to use the food composition of the present invention in the form of food additives, the food composition may be prepared and used in the form of powders or concentrates.

Further, the present invention provides a composition for diagnosing neurodegenerative diseases or depression comprising a compound of Chemical Formula 1 below to which a diagnostic agent or detection agent is bound or a pharmaceutically acceptable salt thereof as an active ingredient.

Further, the present invention provides a composition for diagnosing neurodegenerative diseases or depression consisting of a compound of Chemical Formula 1 below to which a diagnostic agent or detection agent is bound or a pharmaceutically acceptable salt thereof as an active ingredient.

Further, the present invention provides a composition for diagnosing neurodegenerative diseases or depression essentially consisting of a compound of Chemical Formula 1 below to which a diagnostic agent or detection agent is bound or a pharmaceutically acceptable salt thereof as an active ingredient.

[Chemical Formula 1]

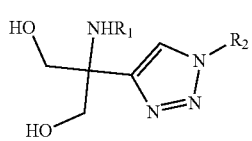

Wherein, $R_1$ is hydrogen; alkyl of 1 to 10 carbon atoms; or substituted or unsubstituted alkylcarbonyl of 1 to 5 carbon atoms, $R_2$ is hydrogen; or alkyl of 1 to 10 carbon atoms, alkenyl of 2 to 10 carbon atoms, or alkynyl of 2 to 10 carbon atoms, and the defined alkyl, alkenyl, alkynyl or alkylcarbonyl each contains or does not contain radioactive isotopes.

Medical imaging tests greatly contribute to the diagnosis and treatment of patients. Recently, with the introduction of reporter gene technology, molecular imaging capable of imaging changes in molecular and cellular levels in vivo has attracted attention. Molecular imaging is a non-invasive method of imaging life phenomena in cellular or molecular units of living organisms and may help in diagnosing diseases by imaging minute functional differences in an initial state where no anatomical changes have occurred due to the disease. Therefore, the molecular imaging is to detect and treat pre-disease conditions early, present a new possibility in the development of therapeutic drugs, and evaluate a response after treatment early to perform appropriate customized treatments for each patient while minimizing toxicity from treatment.

As a test method for obtaining such an image, the diagnostic composition of the present invention may be used as a probe in imaging such as single photon emission computed tomography (SPECT) and positron emission tomography (PET) using radioactive elements. Molecular imaging using nuclear medicine techniques such as SPECT and PET has been developed at a very rapid rate to evaluate functions of the central nervous system, and is actually technology useful for basic medical researches and clinical practices. In particular, research to develop a radioactive probe for PET for imaging a causative agent of neurodegenerative diseases such as Alzheimer's disease has been actively conducted.

According to an embodiment of the present invention, it was confirmed that the compound of Chemical Formula 1 above has a very excellent activity of specifically and directly binding to an ASM protein (Neurobiology of Aging 31 (2010) 398-408, SCIENTIFIC REPORT(2018) 8:3071) known to be increased in expression in the brain of patients with neurodegenerative diseases such as Alzheimer's and multiple sclerosis.

Therefore, the compound represented by Chemical Formula 1 above to which the diagnostic agent or detection agent is bound is directly administered in vivo, or treated to a biological tissue sample, a plasma fluid, or a body fluid as an in vitro biological substance, and thus may be usefully used as a diagnostic substance for tracking and quantifying an ASM protein, and furthermore, be usefully used as a diagnostic substance for diagnosing neurodegenerative diseases caused by over-expression of ASM.

In the present invention, non-limiting examples of the diagnostic agent/detection agent include radioisotopes, dyes (e.g., biotin-streptavidin complex), contrast agents, fluorescent compounds or fluorescent proteins, and magnetic resonance imaging (MRI) contrast enhancers (paramagnetic ions). Preferably, the diagnostic agent includes radioisotopes, magnetic resonance imaging (MRI) contrast enhancers, and fluorescent compounds. In order to load the compound of Chemical Formula 1 above of the present invention with a radioactive metal or paramagnetic ion, it may also be necessary to react with a reactant having multiple dechelating groups binding ions and an attached long tail. The tail may be an Induced or inducible chain having a pendant group capable of binding to a polymer such as polylysine and polysaccharide, or a chelating group such as ethylenediaminetetraacetic acid (EDTA), diethylenetriaminepentaacetic acid (DTPA), porphyrin, polyamine, crown ether, bis-thiosemicarbazone, and polyoximes and having a group known to be useful for the above purposes. The chelate may bind to the compound of Chemical Formula 1 above using standard chemistry. The chelate may be normally linked to the compound of Chemical Formula 1 above by a group capable of forming a bond to a molecule with minimal loss of immunoreactivity and minimal aggregate and/or internal crosslinking.

The fluorescent substance for the diagnosis and detection may be fluorescent compounds such as rhodamine, Alexa derivatives, cyanine derivatives, FAM, TAMRA, FITC, PE, PerCP, APC, and coumarin or derivatives thereof, or fluorescent proteins such as GFP, eGFP, CFP, eCFP, YFP, RFP, etc., but is not limited thereto. Preferably, the fluorescent substance may be cyanine derivatives such as Cy3, Cy3.5, Cy5, Cy5.5 and Cy7. The fluorescent substance may bind to the compound of Chemical Formula 1 above of the present invention directly or through a linker.

In particular, useful metal-chelate combinations include diagnostic isotopes and 2-benzyl-DTPA and monomethyl and cyclohexyl analogs thereof used in a general energy range of 60 to 4,000 keV. For example, radioisotopes used as an imaging agent and/or a therapeutic agent include 125I, 131I, 123I, 124I, 62Cu, 64Cu, 67Cu, 186Re, 188Re, 82Rb, 177Lu, 18F, 153Sm, 213Bi, 111In, 67Ga, 68Ga, 89Sr, 169Er, 192Ir, 111In, 90Y, 99mTc, 94 mTc, 11C, 13N, 15O, 76Br, etc. Representative transition metal ions such as manganese (Mn), iron (Fe), and gadolinium (Gd) among non-radioactive metals are paramagnetic materials and useful for MRI. However, since the ions and radioactive isotopes are highly self-toxic, the ions and radioactive isotopes may be used in combination with a chelating agent or the like. The chelating agent may be combined with a macrocyclic chelating agent such as DTPA, NOTA, DOTA, MS325, HPDO3A, EDTA, NTA and TETA, depending on a type of metal, and the complex may be used by binding to the compound of Chemical Formula 1 above of the present invention. Preferably, the chelating agent may be used with radionuclides of gallium, yttrium and copper, respectively, and the metal-chelate complex may be prepared very stably by fitting a ring size to a target metal. Cyclic chelates such as macrocyclic polyethers useful for stably binding to nuclides such as 223Ra used in radiation and imaging technology (RAIT) may also be included in the scope of the present invention.

On the other hand, when the diagnostic agent or detection agent is not bound to the compound of Chemical Formula 1 above of the present invention, the carbon atom of the alkyl, alkenyl, alkynyl, or alkylcarbonyl may be a radioactive isotope [11C].

The present invention provides a use of a compound of Chemical Formula 1 below or a pharmaceutically acceptable salt thereof for preparing an agent for preventing or treating neurodegenerative diseases or depression.

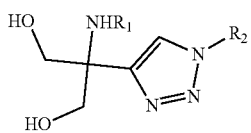

[Chemical Formula 1]

Wherein,

R₁ is hydrogen; alkyl of 1 to 10 carbon atoms; or substituted or unsubstituted alkylcarbonyl of 1 to 5 carbon atoms, and R₂ is hydrogen; or alkyl of 1 to 10 carbon atoms, alkenyl of 2 to 10 carbon atoms, or alkynyl of 2 to 10 carbon atoms.

Further, the present invention provides a method for preventing or treating neurodegenerative diseases or depression comprising administering an effective dose of a composition containing the compound of Chemical Formula 1 above or a pharmaceutically acceptable salt thereof as an active ingredient to a subject in need thereof.

The present invention provides a use of a compound of Chemical Formula 1 below to which a diagnostic agent or detection agent is bound or a pharmaceutically acceptable salt thereof for preparing an agent for diagnosing neurodegenerative diseases or depression.

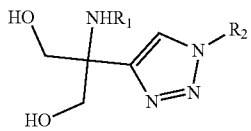

[Chemical Formula 1]

Wherein,

R₁ is hydrogen; alkyl of 1 to 10 carbon atoms; or substituted or unsubstituted alkylcarbonyl of 1 to 5 carbon atoms, R₂ is hydrogen; or alkyl of 1 to 10 carbon atoms, alkenyl of 2 to 10 carbon atoms, or alkynyl of 2 to 10 carbon atoms, and the defined alkyl, alkenyl, alkynyl or alkylcarbonyl each contains or does not contain radioactive isotopes.

Further, the present invention provides a method for diagnosing neurodegenerative diseases or depression comprising administering an effective dose of a composition containing the compound of Chemical Formula 1 above to which a diagnostic agent or detection agent is bound or a pharmaceutically acceptable salt thereof as an active ingredient to a subject suspected of neurodegenerative diseases or depression.

The term 'effective dose' of the present invention refers to an amount which exhibits effects of improving, treating, preventing, detecting, and diagnosing neurodegenerative diseases or depression, or an effect of inhibiting or alleviating neurodegenerative diseases or depression when administered to a subject. The 'subject' may be animals, preferably, mammals, particularly animals including humans and may also be cells, tissues, and organs derived from animals. The subject may be a patient requiring the effects.

The term 'treatment' of the present invention comprehensively refers to improving neurodegenerative diseases or depression, or symptoms of neurodegenerative diseases or depression, and may include treating or substantially preventing neurodegenerative diseases or depression, or improving the conditions thereof and include alleviating, treating or preventing a symptom or most of symptoms derived from neurodegenerative diseases or depression, but is not limited thereto.

The term 'comprising' of the present invention is used in the same manner as 'containing' or 'characterizing', and does not exclude additional ingredients or steps of the method which are not mentioned in the composition or the method. The term 'consisting of' means excluding additional elements, steps or ingredients, etc., which are not separately mentioned. The term 'essentially consisting of' means including ingredients or steps that do not substantially affect basic properties thereof in addition to the described ingredients or steps within the scope of the composition or the method.

Advantageous Effects

The ASM inhibitory compound of Chemical Formula 1 of the present invention directly binds to the ASM protein to have an excellent effect of inhibiting ASM and therapeutic effects such as reducing Aβ plaques in an Alzheimer's brain environment, alleviating neuroinflammation, improving memory and anxiety, etc. In addition, the ASM inhibitory compound has a very high distribution in the brain and very excellent metabolic stability by liver microsomes. Accordingly, the ASM inhibitory compound of Chemical Formula 1 of the present invention may be very usefully used to develop an agent for preventing or treating neurodegenerative diseases including Alzheimer's disease, and a composition for diagnosing neurodegenerative diseases. In addition, as previously reported that inhibition of ASM is effective in relieving depression, a novel compound of inhibiting ASM of Chemical Formula 1 of the present invention may be usefully used as an agent for preventing or treating neurological diseases including depression.

Substance name SCNPA501, Compound name 2-amino-2-(1-hexyl-1H-1,2,3-triazol-4-yl)propane-1,3-diol, Substance name SCNPA401, Compound name 2-amino-2-(1-heptyl-1H-1,2,3-triazol-4-yl)propane-1,3-diol, Substance name SCNPA301, Compound name 2-amino-2-(1-octyl-1H-1,2,3-triazol-4-yl)propane-1,3-diol, Substance name SCNPA201, Compound name 2-amino-2-(1-nonanyl-1H-1,2,3-triazol-4-yl)propane-1,3-diol, Substance name SCNPA101, Compound name 2-amino-2-(1-dodecyl-1H-1,2,3-triazol-4-yl)propane-1,3-diol.

Figure 2A:
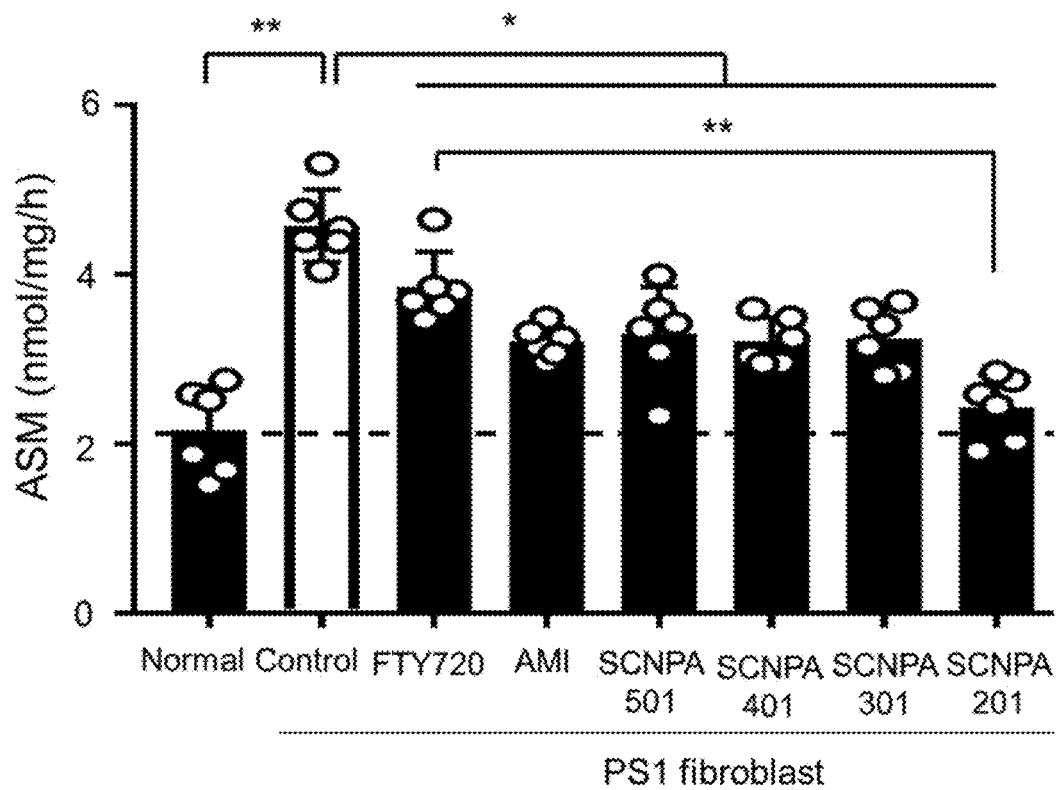
Figures 2B, 3A:
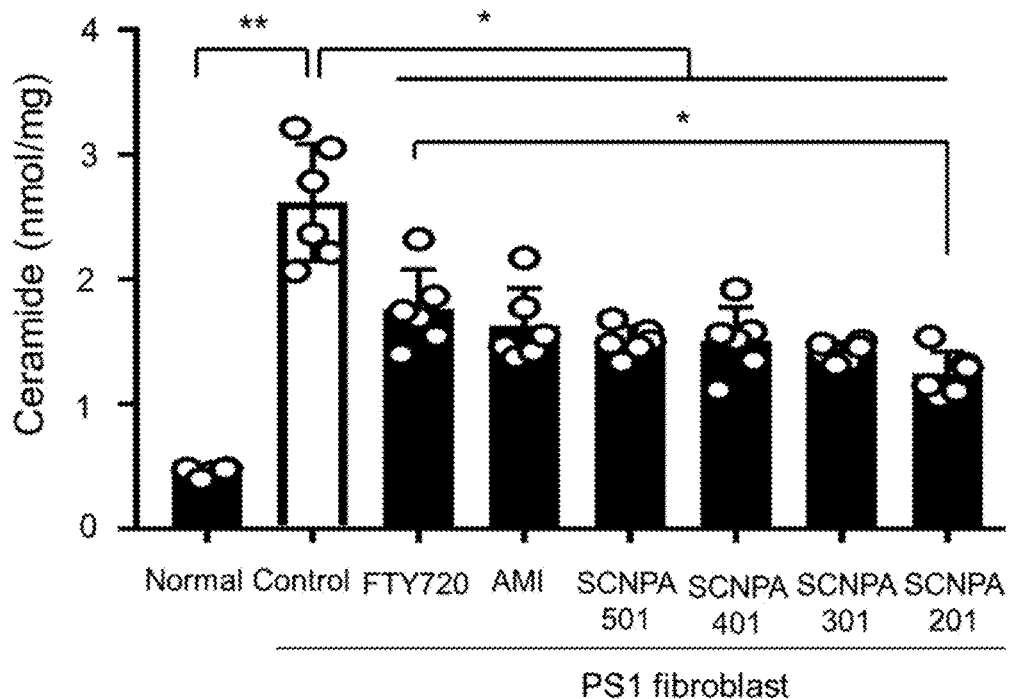

FIGS. 2a and 2b are diagrams illustrating changes in ASM activity shown after treatment of ASM inhibitory compounds and FTY720 in PS1 fibroblasts of an Alzheimer's patient (FIG. 2a) and amounts of Ceramide which is a product generated by ASM (FIG. 2b) (n=6/group).

Figure 3B:
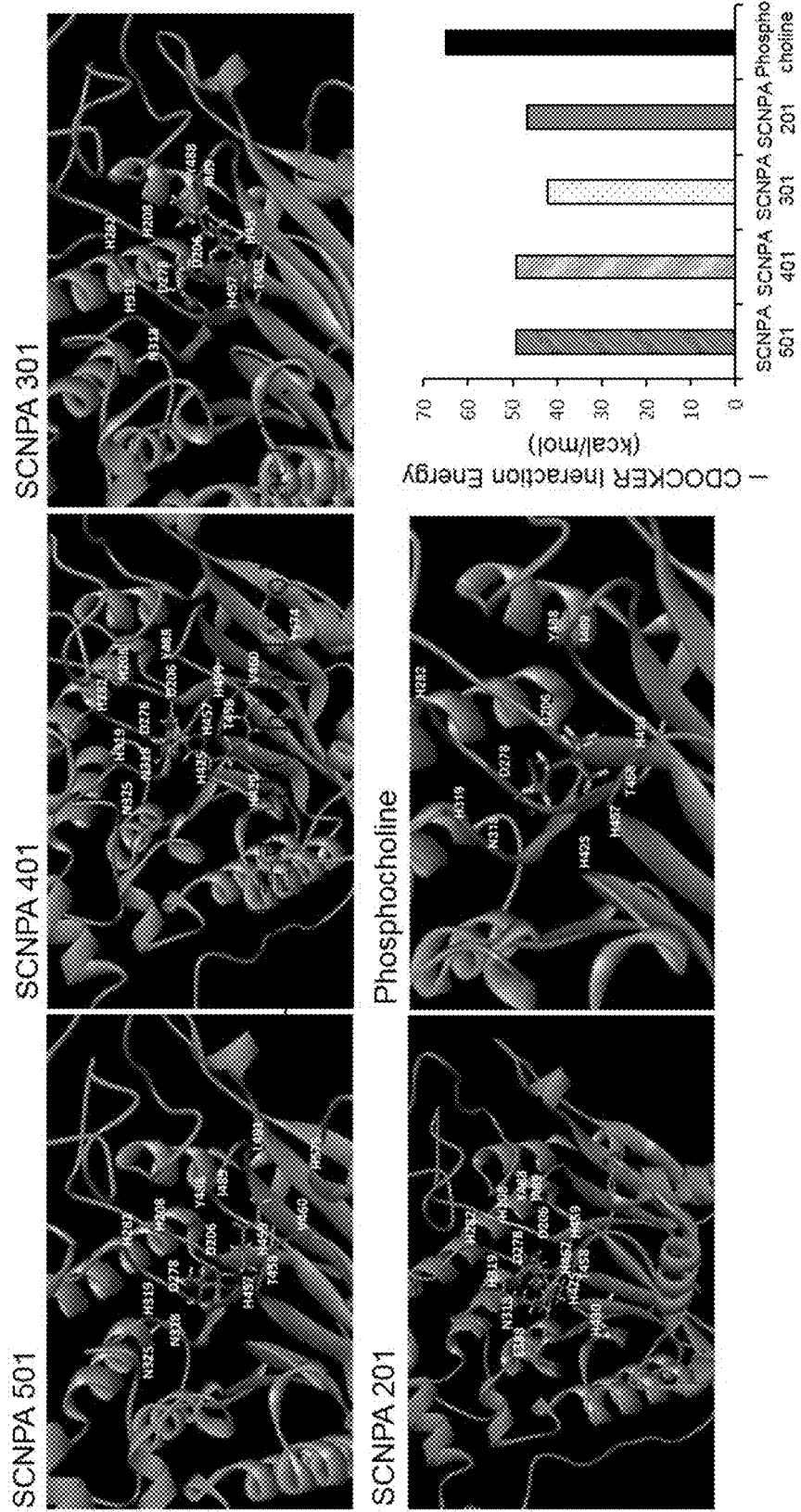

FIGS. 3a and 3b are a diagram of digitizing concentrations at which ASM inhibitory compounds may inhibit the activity of ASM by 50% (FIG. 3a) and a diagram of directly binding to an ASM active site and digitizing binding energy thereto (FIG. 3b).

Figure 4A:
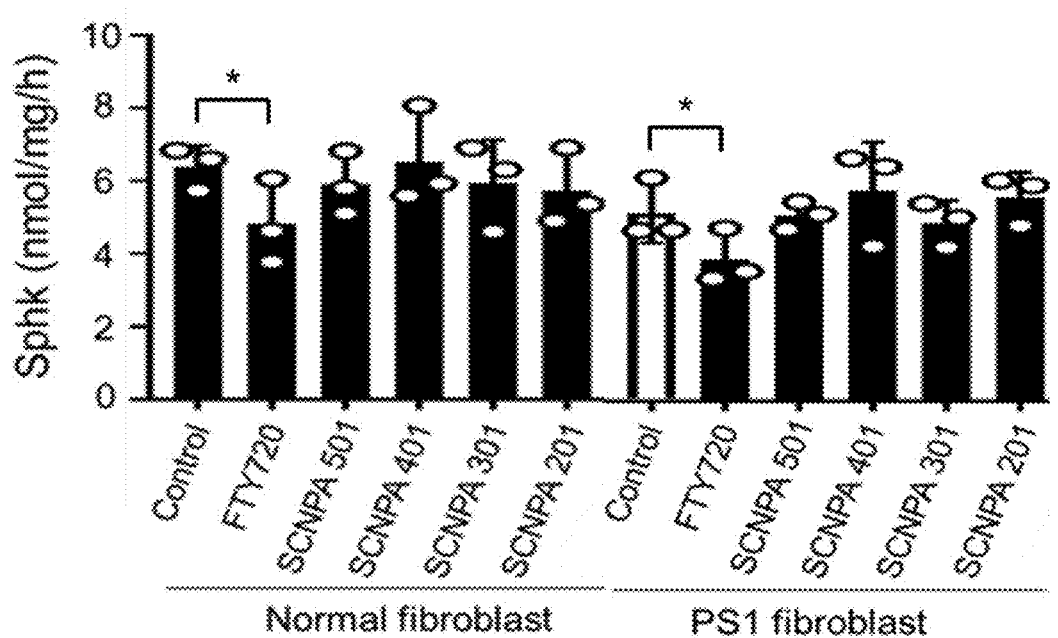
Figure 4B:
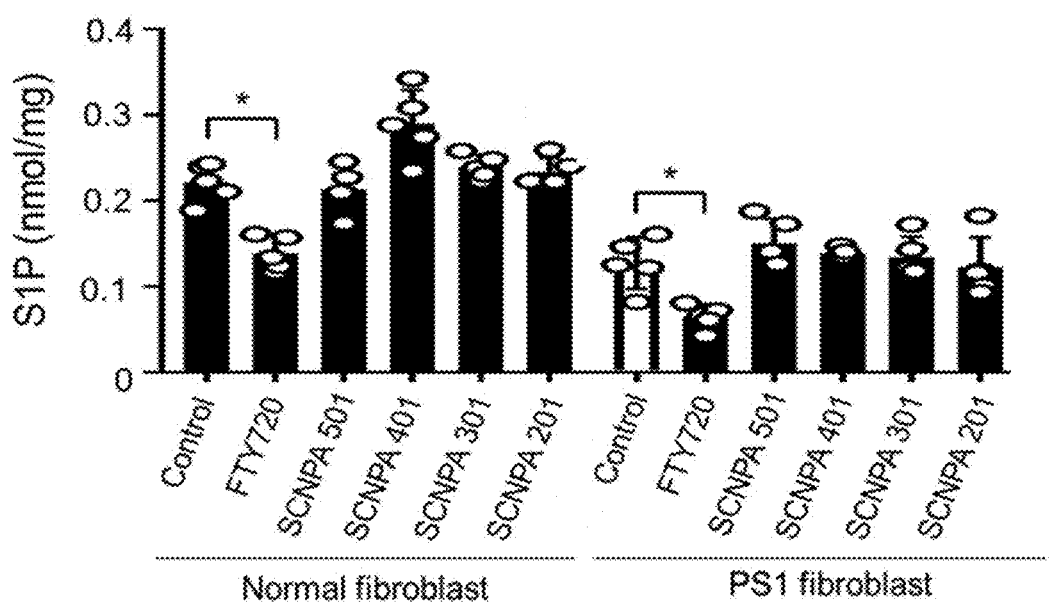
Figure 4C:
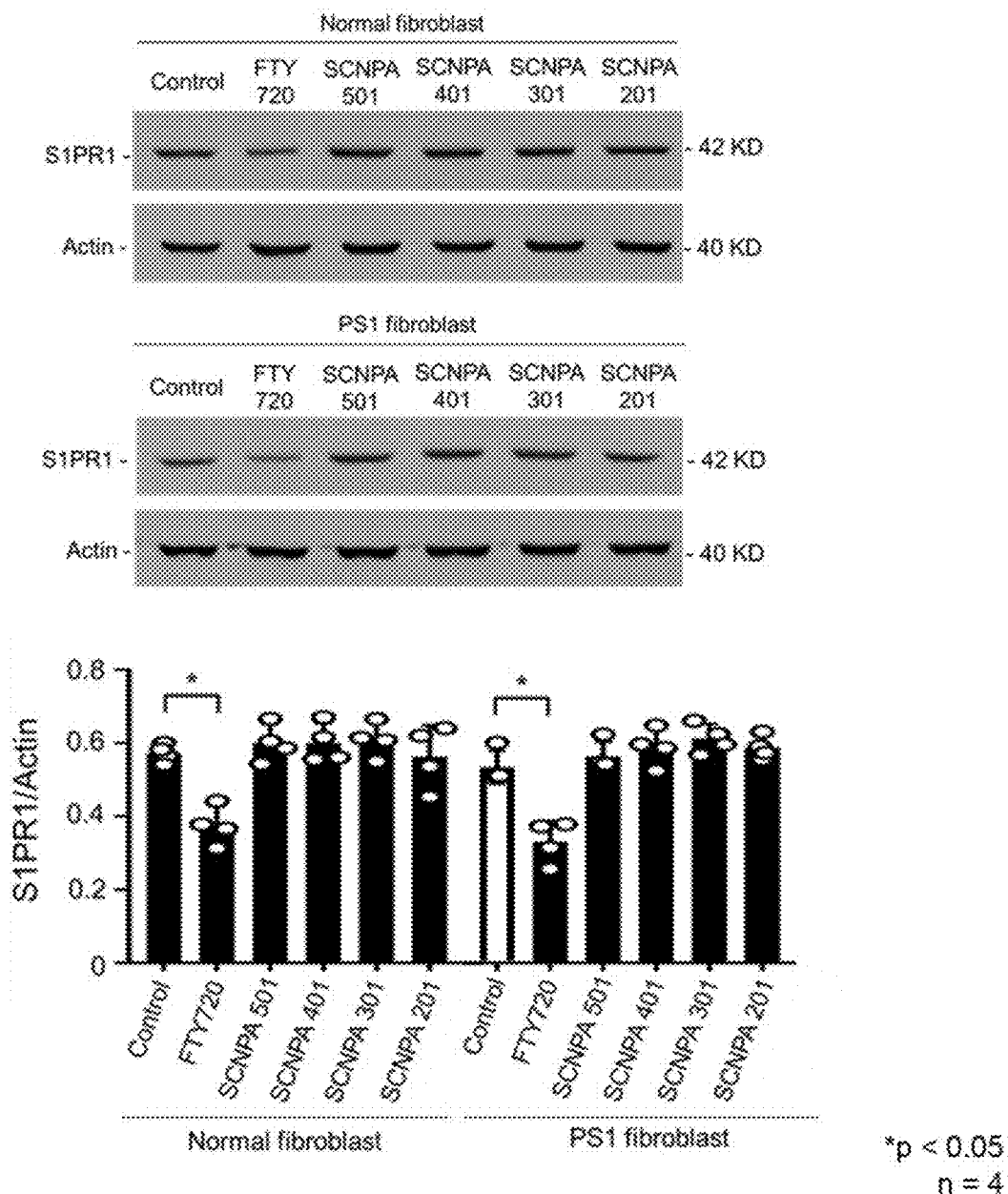

FIGS. 4a to 4c are diagrams of confirming whether ASM inhibitory compounds inhibit Sphk activity (FIG. 4a) and S1P (FIG. 4b), and whether to induce reduction of expression of a S1P receptor 1 (S1PR1) (FIG. 4c) (n=3-5/group).

Figure 5A:
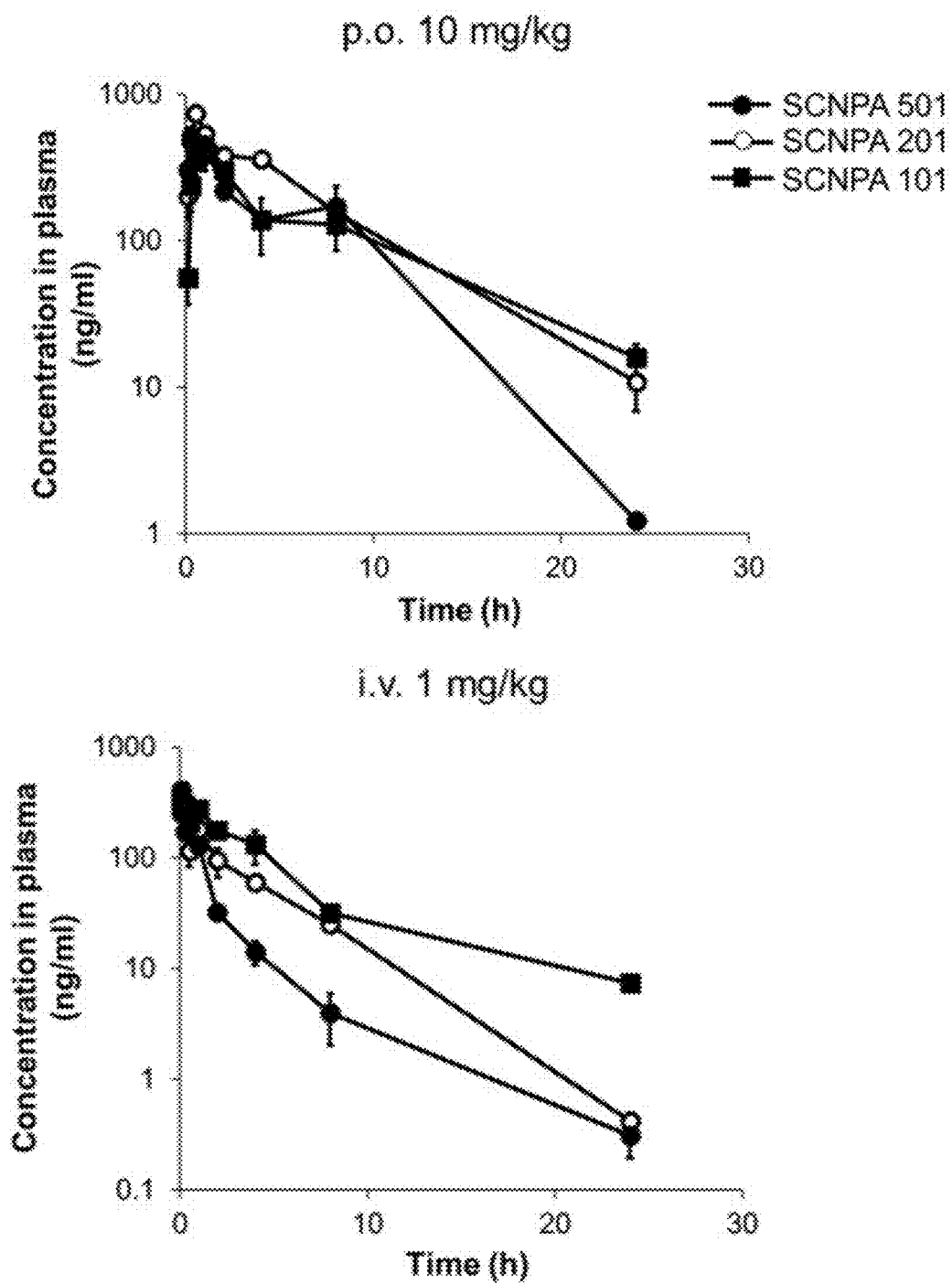

FIGS. 5a and 5b are diagrams for pharmacokinetic test analysis of ASM inhibitory compounds SCNPA501, SCNPA201, and SCNPA101.

FIG. 5a is a graph showing concentrations in blood of ASM inhibitory compounds SCNPA501, SCNPA201, and SCNPA101 after oral (p.o. 10 mg/kg) or intravenous administration (i.v. 1 mg/kg) in normal mice for each time period (n=3/group).

FIG. 5b illustrates a result of the pharmacokinetic test analysis in blood of ASM inhibitory compounds SCNPA501, SCNPA201, and SCNPA101 after oral (p.o. 10 mg/kg) or intravenous administration (i.v. 1 mg/kg) in normal mice (n=3/group).

Figure 6A:
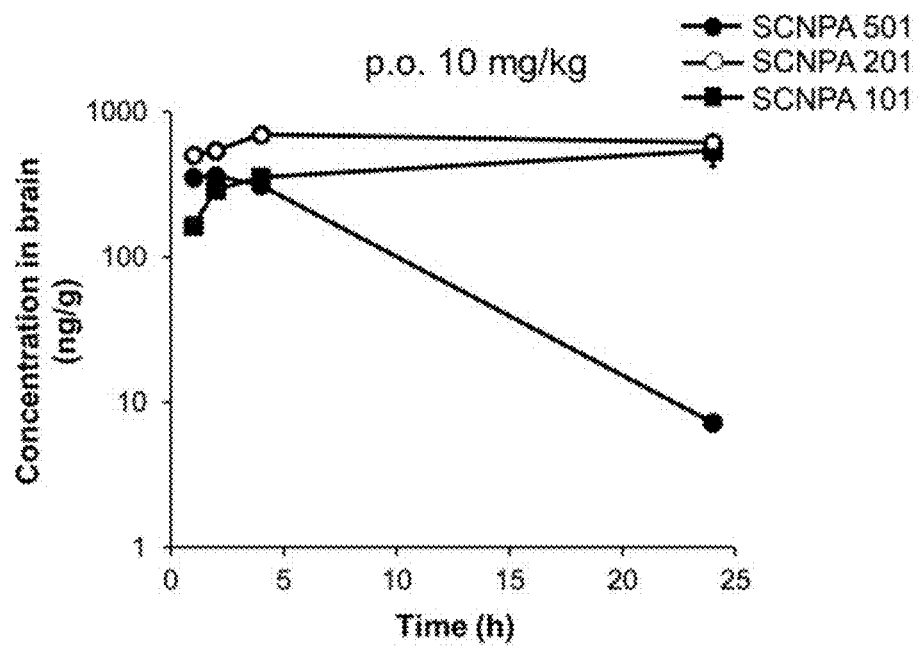
Figure 6A:
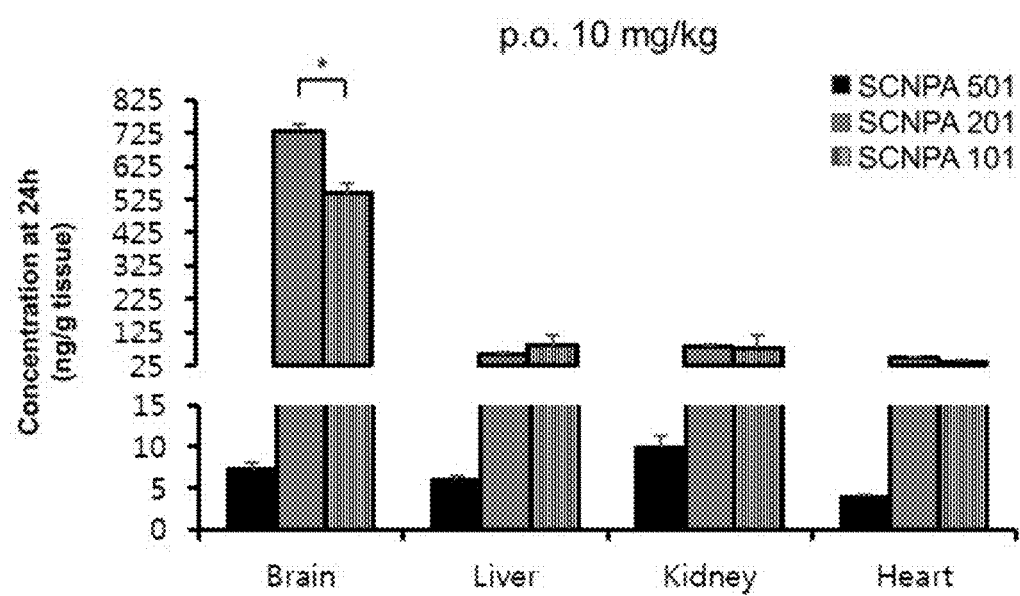

FIGS. 6a and 6b are diagrams of pharmacokinetic test analysis for brain distribution after in vivo injection of ASM inhibitory compounds SCNPA501, SCNPA201, and SCNPA101 (n=3/group).

FIG. 6a illustrates a result (left) showing remaining concentrations in brain of ASM inhibitory compounds SCNPA501, SCNPA201, and SCNPA101 after oral (p.o. 10 mg/kg) for each time period and a result (right) showing remaining concentrations in brain, liver, kidneys, and heart after 24 hours in normal mice (n=3/group).

FIG. 6b illustrates a result of pharmacokinetic test analysis for brain distribution after in vivo injection of ASM inhibitory compounds SCNPA501, SCNPA201, and SCNPA101 (n=3/group).

Figure 7A:
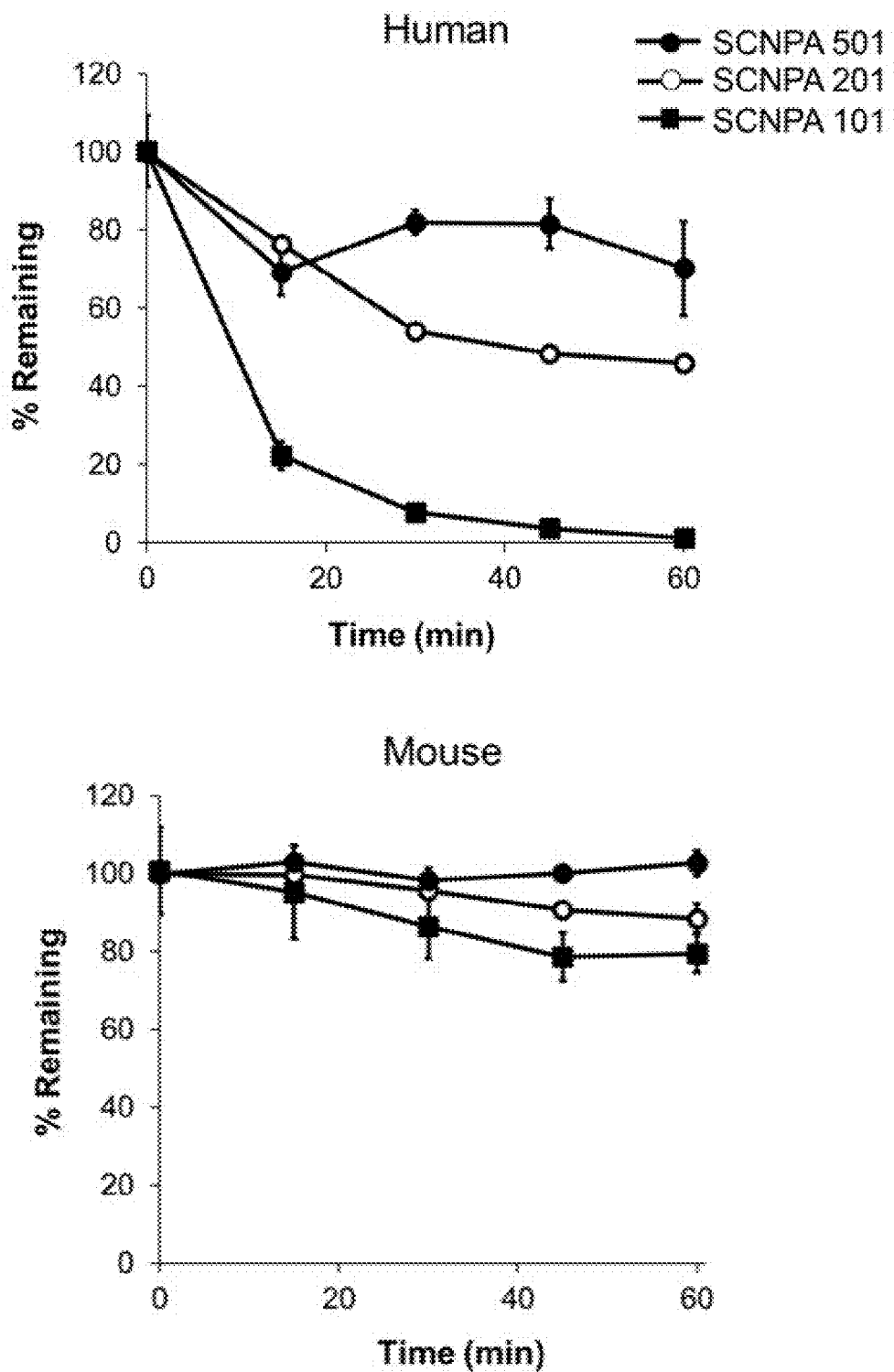
Figures 7B, 8:
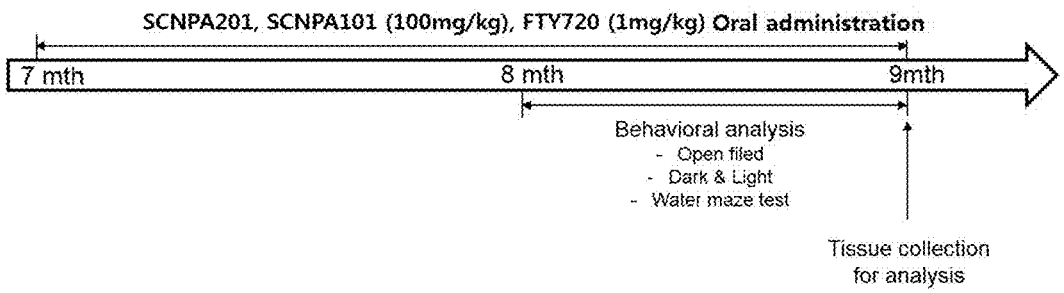

FIGS. 7a and 7b are diagrams illustrating the stability of ASM inhibitory compounds SCNPA501, SCNPA201, and SCNPA101 in human or mouse liver microsomes.

FIG. 7a is a diagram illustrating percentages of remaining amounts for each time period after treating ASM inhibitory compounds SCNPA501, SCNPA201, and SCNPA101 in human or mouse liver microsomes (n=3/group).

FIG. 7b illustrates a result showing percentages of remaining amounts after 30 minutes and half-life after treating ASM inhibitory compounds SCNPA501, SCNPA201, and SCNPA101 in human or mouse liver microsomes (n=3/group).

FIG. 8 is a diagram illustrating an outline of a test conducted to confirm an effect of ASM inhibition on Alzheimer's disease by injection of an ASM inhibitory compound SCNPA201, SCNPA101 or FTY720.

Figure 9B:
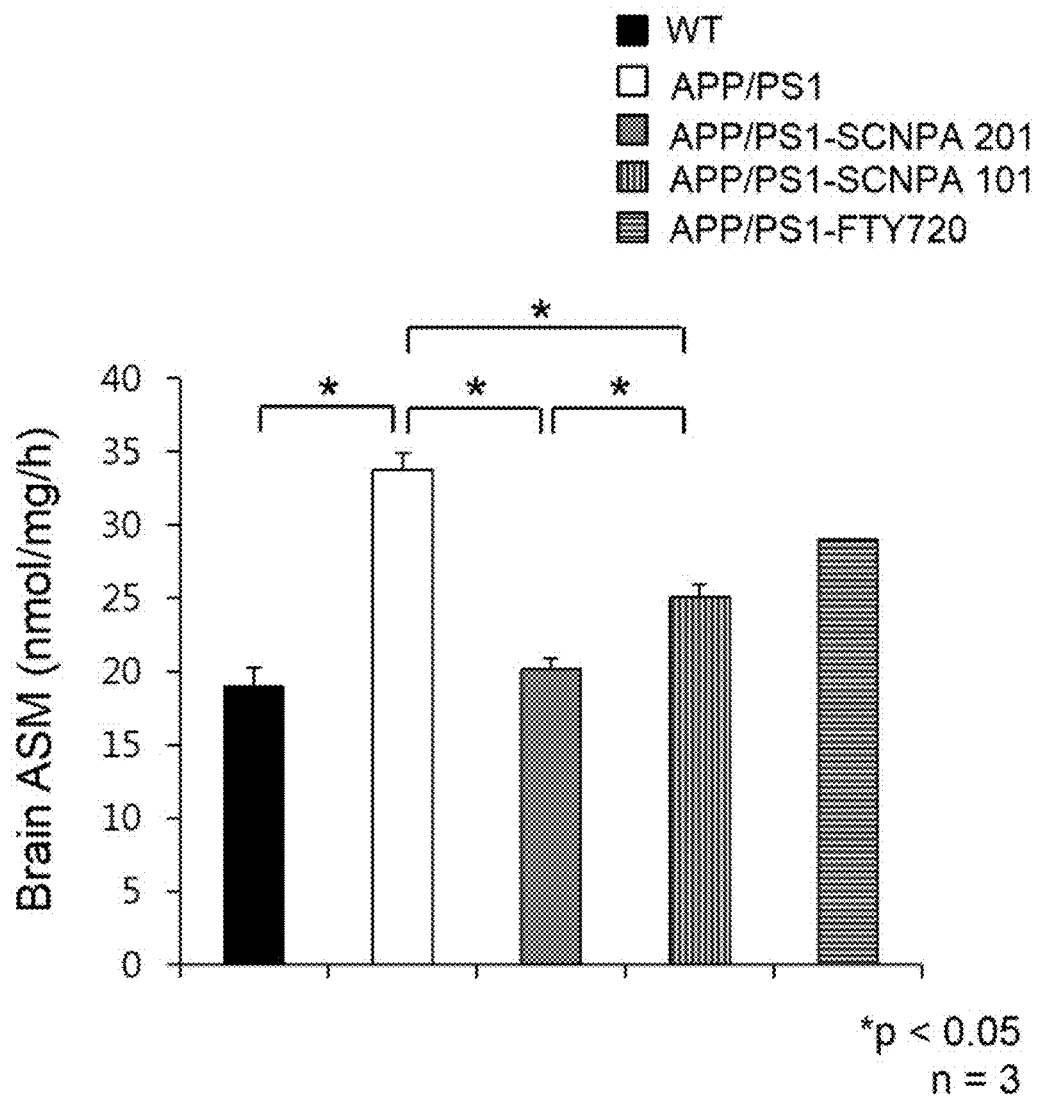

FIGS. 9a and 9b are diagrams illustrating changes in ASM concentration in serum (FIG. 9a) and brain tissue (FIG. 9b) of mice after administration of an ASM inhibitory compound SCNPA201, SCNPA101 or FTY72 to an Alzheimer's animal models (n=4 to 6/group) (WT: wild type, APP/PS1: Alzheimer's animal model).

Figure 10:
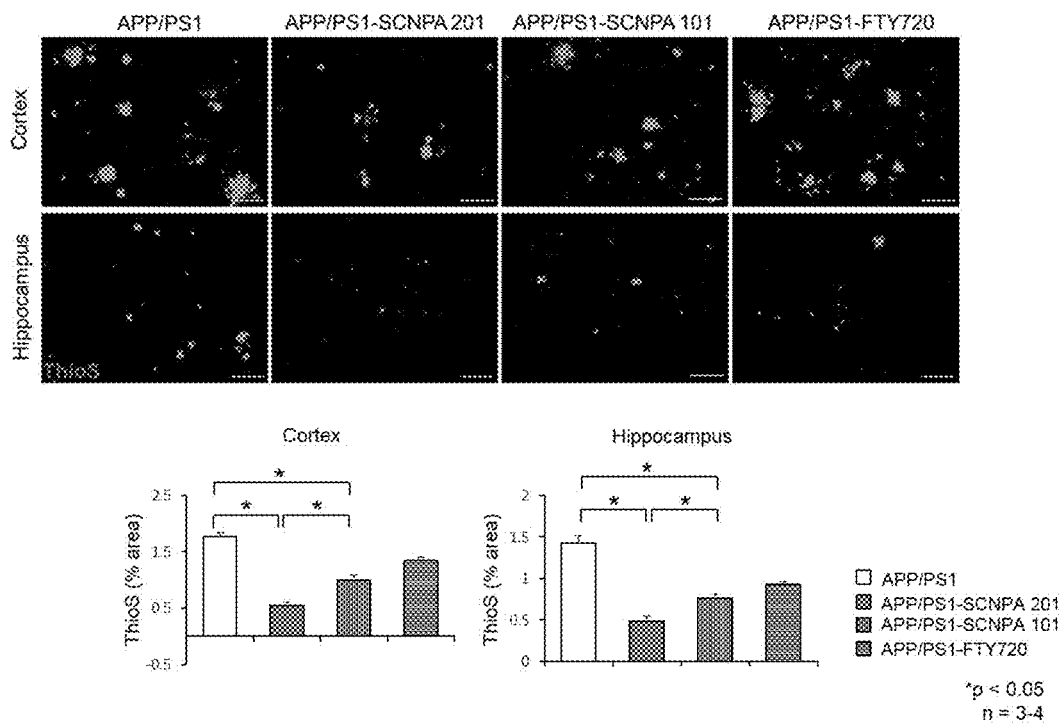

FIG. 10 illustrates results of immunofluorescence staining of Thioflavin S (ThioS, protofibril amyloid beta plaques) and quantifying areas occupied by the protofibril amyloid beta plaques in the medulla and hippocampus of an Alzheimer's animal model administered with an ASM inhibitory compound SCNPA201, SCNPA101 or FTY72 (n=3 to 4/group) (WT: wild type, APP/PS1: Alzheimer's animal model).

Figure 11A:
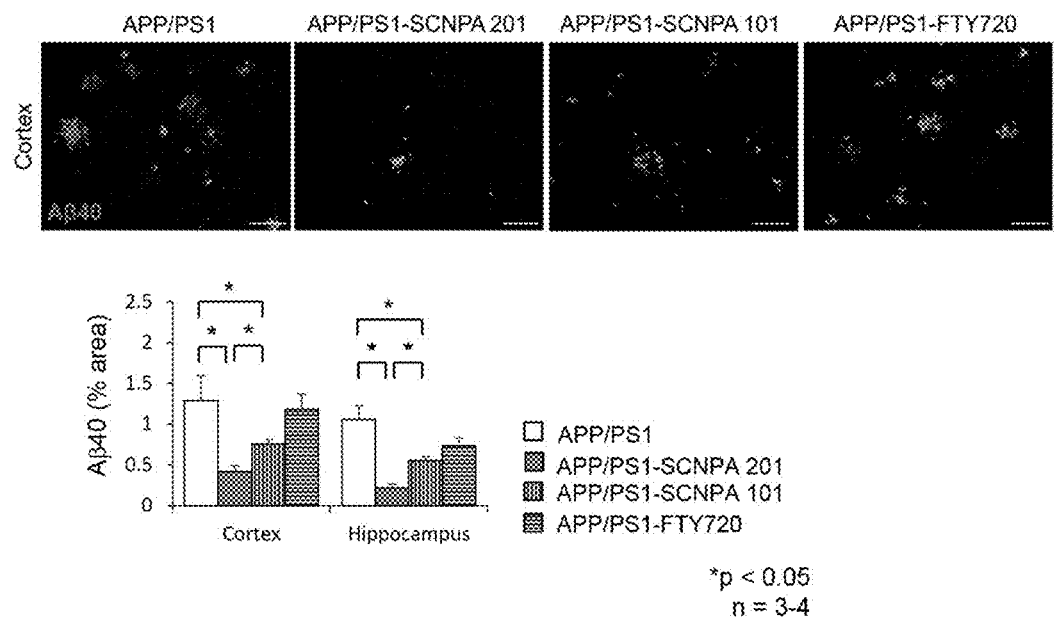
Figure 11B:
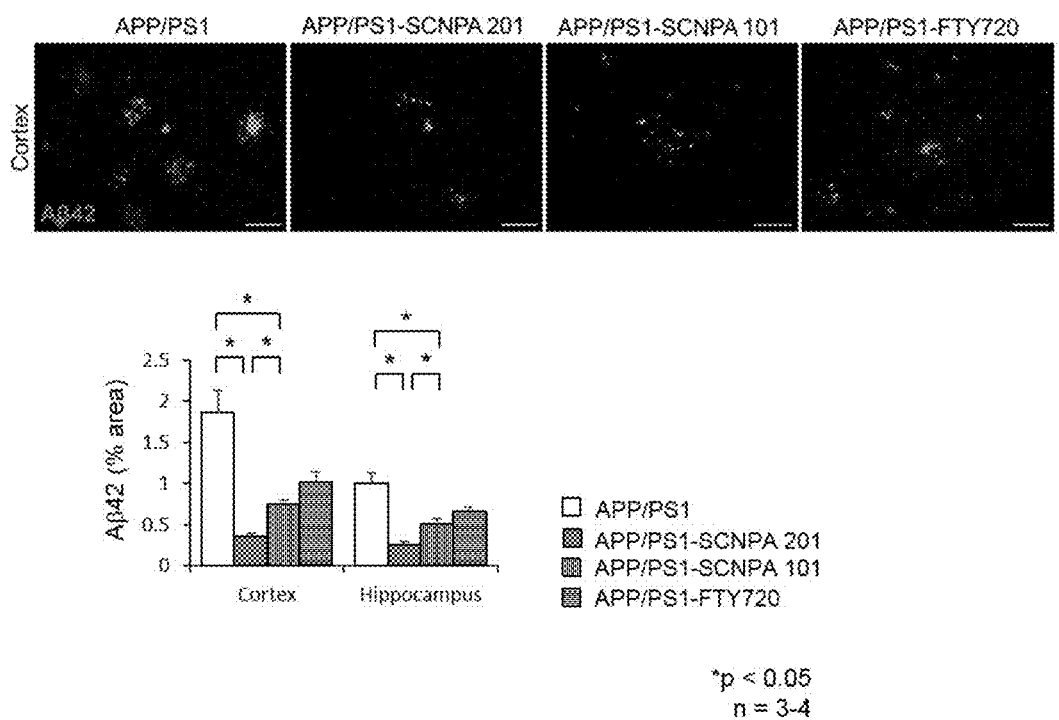

FIGS. 11a and 11b illustrate results of immunofluorescence staining of accumulation of Aβ40 (FIG. 11a) or Aβ42 (FIG. 11b) and quantifying the accumulation in the medulla and hippocampus of an Alzheimer's animal model administered with an ASM inhibitory compound SCNPA201, SCNPA101 or FTY72 (n=3 to 4/group) (WT: wild type, APP/PS1: Alzheimer's animal model).

Figure 12A:
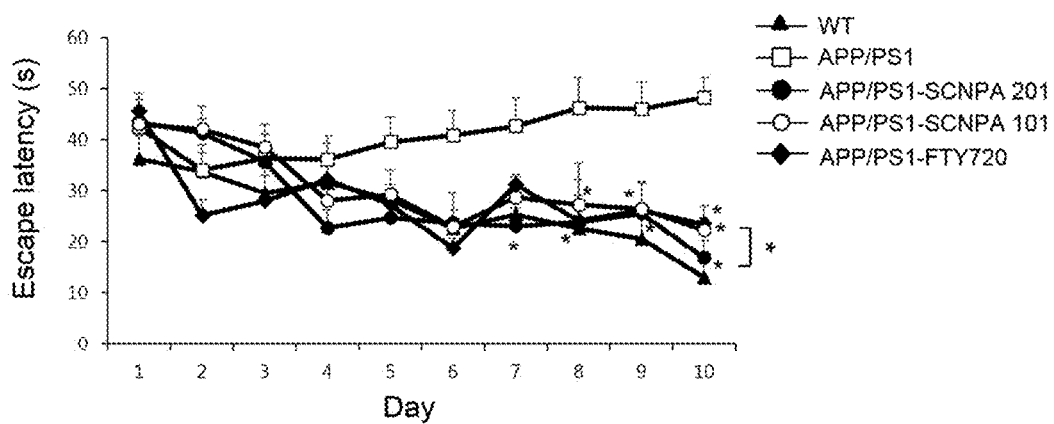
Figure 12B:
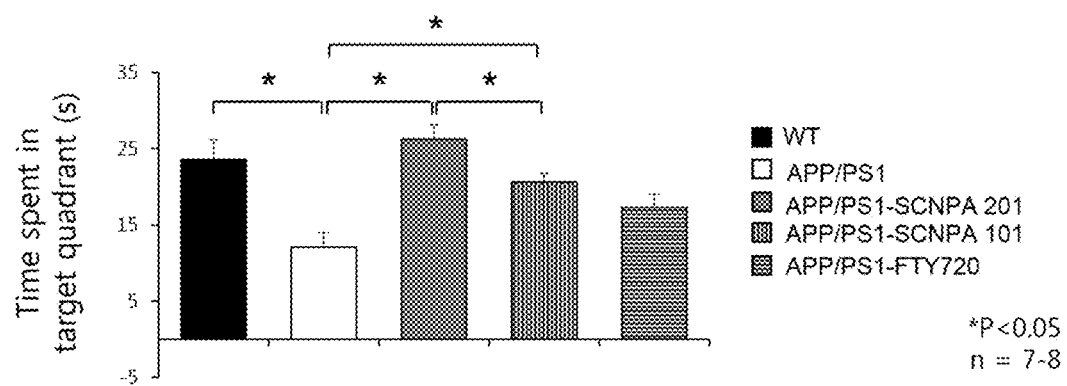
Figure 12C:
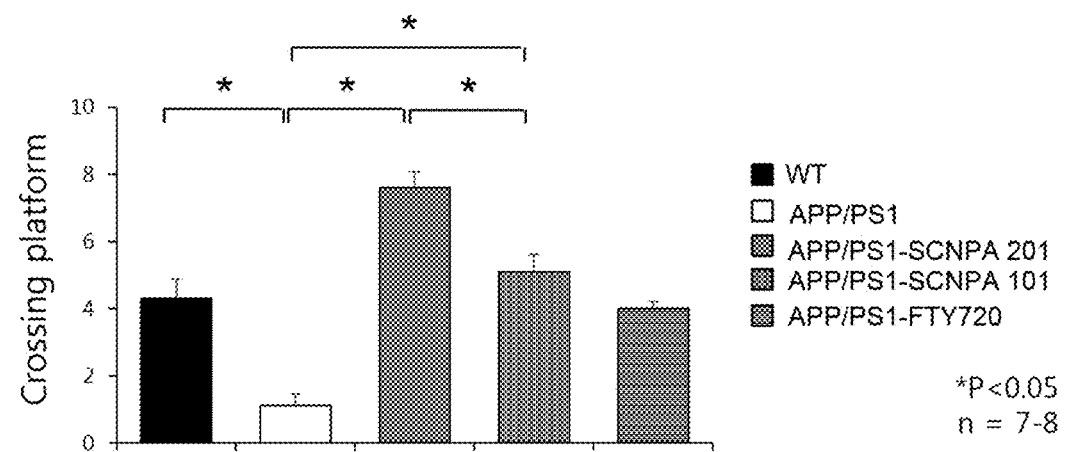

FIGS. 12a to 12c illustrate results indicating the degree of recovery of learning and cognitive functions in an Alzheimer's animal model administered with an ASM inhibitory compound SCNPA201, SCNPA101 or FTY72 (wild-type mouse (n=8), APP/PS1 mouse supplied with water of ASM inhibitory compound SCNPA201 (n=7), APP/PS1 mouse supplied with water of ASM inhibitory compound SCNPA101 (n=8), APP/PS1 mouse supplied with water of FTY720 (n=7) or APP/PS1 mouse not supplied (n=8)).

FIG. 12a illustrates results of evaluating learning and memory through a Morris Water Maze test in a wild-type mouse, an APP/PS1 mouse supplied with water of an ASM inhibitory compound SCNPA201, an APP/PS1 mouse supplied with water of an ASM inhibitory compound SCNPA101, an APP/PS1 mouse supplied with water of FTY720 or an APP/PS1 mouse not supplied.

FIG. 12b illustrates a result showing a time staying in a target platform on day 11 of the test.

FIG. 12c illustrates the number of times of entering into a target area of the target platform on day 11 of the test.

Figure 13A:
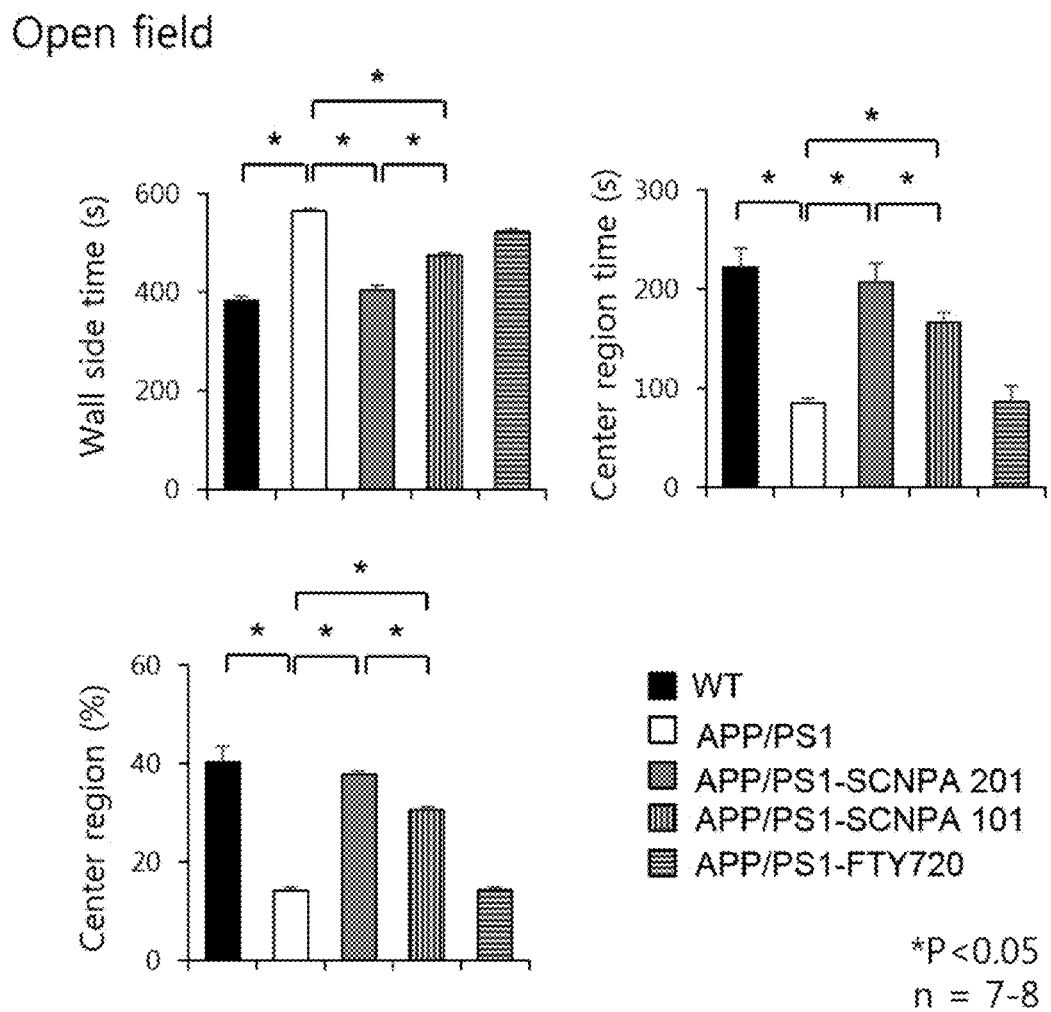
Figure 13B:
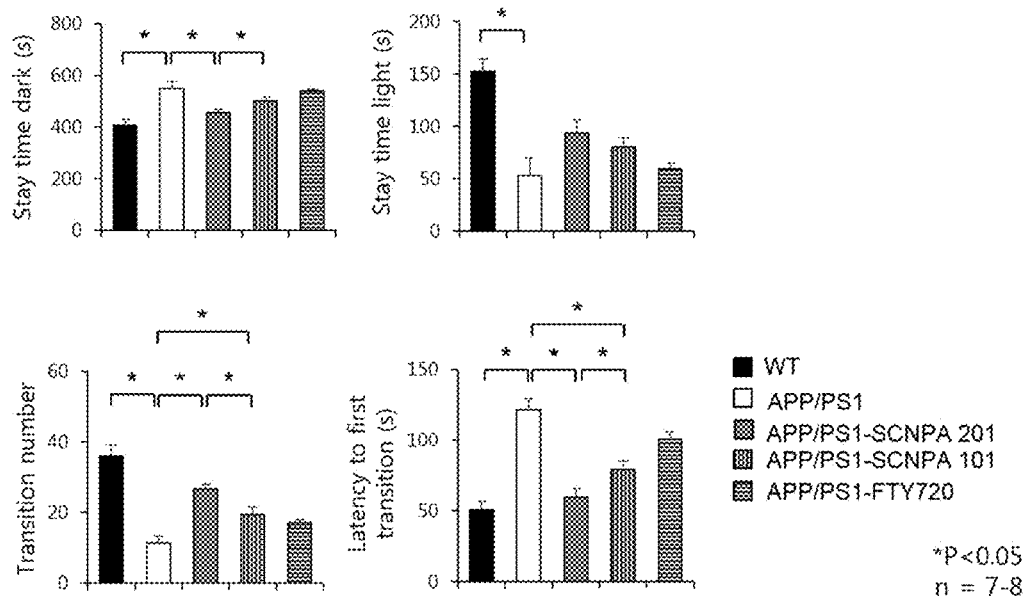

FIGS. 13a and 13b illustrate results indicating improved activity and anxiety in an Alzheimer's animal model administered with an ASM inhibitory compound SCNPA201, SCNPA101 or FTY72 (wild-type mouse (n=8), APP/PS1 mouse supplied with water of ASM inhibitory compound SCNPA201 (n=7), APP/PS1 mouse supplied with water of ASM inhibitory compound SCNPA101 (n=8), APP/PS1 mouse supplied with water of FTY720 (n=7) or APP/PS1 mouse not supplied (n=8)).

FIG. 13a illustrates a result showing a time spent on a wall side and a center region by a mouse and a ratio of the center region during an open field test.

FIG. 13b illustrates a result of measuring times spent in dark and light places by a mouse in a dark & light test and a result of measuring the number of reciprocating dark and light places by a mouse and a first transition time from the dark place to the light place by the mouse during the test.

Figure 14A:
Figure 14A:
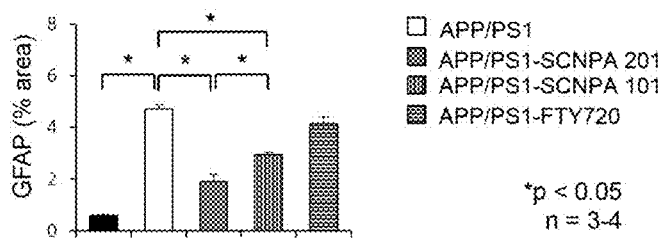
Figure 14B:
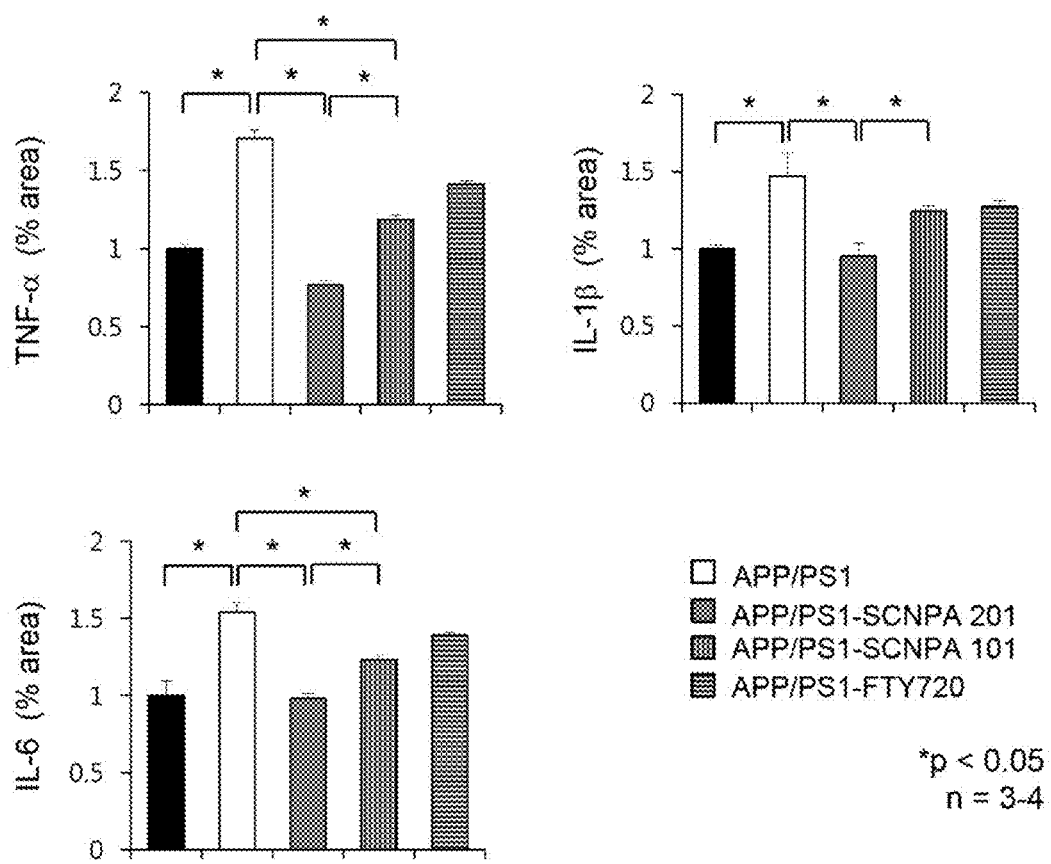

FIGS. 14a and 14b illustrate results of confirming that increased neuroinflammation is reduced by injection of an ASM inhibitory compound SCNPA201 in an Alzheimer's animal model (WT: wild type, AD: Alzheimer's animal model (APP/PS1 mouse)).

FIG. 14a illustrates a result of quantifying percentages of astrocytes (GFAP) in the medulla of a wild-type mouse and an Alzheimer's animal model administered with an ASM inhibitory compound SCNPA201, SCNPA101 or FTY720 (n=3 to 4/group).

FIG. 14b illustrates results of evaluating mRNA expression levels of inflammatory markers TNF-α, IL-1β, and IL-6 in the medulla of an Alzheimer's animal model administered with an ASM inhibitory compound SCNPA201, SCNPA101 or FTY720 (n=3 to 4/group).

MODES FOR THE INVENTION

Hereinafter, the present invention will be described in detail.

However, the following Examples are just illustrative of the present invention, and the contents of the present invention are not limited to the following Examples.

Test Materials and Test Methods

0. Synthesis of Compounds

Substance name SCNPA501, Compound name 2-amino-2-(1-hexyl-1H-1,2,3-triazol-4-yl)propane-1,3-diol, Substance name SCNPA401, Compound name 2-amino-2-(1-heptyl-1H-1,2,3-triazol-4-yl)propane-1,3-diol, Substance name SCNPA301, Compound name 2-amino-2-(1-octyl-1H-1,2,3-triazol-4-yl)propane-1,3-diol, Substance name SCNPA201, Compound name 2-amino-2-(1-nonanyl-1H-1,2,3-triazol-4-yl)propane-1,3-diol, and Substance name SCNPA101, Compound name 2-amino-2-(1-dodecyl-1,2,3-triazol-4-yl)propane-1,3-diol were prepared through the following series of processes. For example, a detailed preparation process of Substance name SCNPA201 and Compound name 2-amino-2-(1-nonanyl-1H-1,2,3-triazol-4-yl)propane-1,3-diol was as follows.

0-1. Reaction Formula 1, Synthesis of 1-azidononane

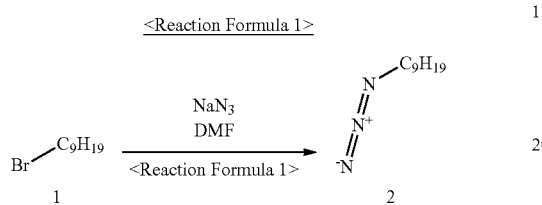

In order to synthesize 1-azidononane of Reaction Formula 1, sodium azide (12.6 g, 190 mmol, 2 eq) was added to a solution of 1-bromononane (20 g, 96 mmole) of Chemical Formula 1 in DMF (200 ml). The mixture was stirred at room temperature for 3 days and diluted with EA (30 ml)/n-hexane (100 ml). The mixture was washed with $H_2O$ (600 ml×2), dried on $MgSO_4$ and concentrated to obtain 1-azidononane of Chemical Formula 2 (16 g, 98%).

$^1$H NMR (400 MHz, $CDCl_3$): δ 3.25 (t, 2H), 1.59 (pentet, 2H), 1.37-1.24 (m, 15H), 0.88 (t, 3H)

0-2. Reaction Formula 2, Synthesis of 2-amino-2-(hydroxymethyl)propane-1,3-diol

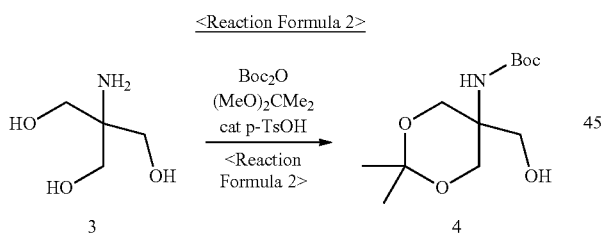

In order to synthesize 2-amino-2-(hydroxymethyl)propane-1,3-diol of Reaction Formula 2, Boc2O (49.5 g, 1.1 eq) was added to a suspension of tris(hydroxymethyl)aminomethane (25.0 g, 0.206 mol) of Chemical Formula 3 in DMF (500 ml). The mixture was stirred at room temperature for 2 hours, and then added with 2,2-dimethoxypropane (30.4 ml, 1.2 eq) and p-TsOH. $H_2O$ (2.0 g, 0.05 eq). The mixture was stirred at room temperature for 18 hours and diluted with Et2O (500 ml). An organic layer was washed with a saturated $NaHCO_3$ solution (300 ml) and salt water (200 ml). The organic layer was dried on $MgSO_4$ and concentrated. A residue was crystallized with n-hexane to obtain tert-butyl 5-(hydroxymethyl)-2,2-dimethyl-1,3-dioxane-5-ylcarbamate of Chemical Formula 4 as a white solid (32.0 g, 59.4%).

$^1$H NMR (600 MHz, $CDCl_3$): δ 5.32 (s, 1H), 3.86-3.80 (m, 4H), 3.73 (s, 2H), 3.68 (s, 1H), 1.46-1.44 (m, 15H)

0-3. Reaction Formula 3, Synthesis of tert-butyl 5-formyl-2,2-dimethyl-1,3-dioxan-5-ylcarbamate

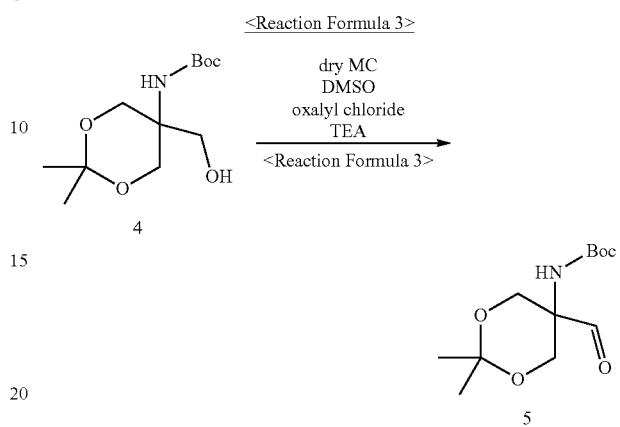

In order to synthesize tert-butyl 5-formyl-2,2-dimethyl-1,3-dioxane-5-ylcarbamate of Reaction Formula 3, first, DMSO (43.7 ml, 5 eq) was mixed with a solution of oxalyl chloride (33.4 ml, 3.17 eq) in dry MC (340 ml) at −78° C. The mixture was stirred for 15 minutes, and then mixed with tert-butyl 5-(hydroxymethyl)-2,2-dimethyl-1,3-dioxane-5-ylcarbamate (32.0 g, 0.123 mol) ml) of Chemical Formula 4 in anhydrous MC (340 ml). The mixture was stirred for 2 hours and then added with Et3N (171 ml, 10 eq). The mixture was stirred for 10 minutes, and then a cooling tank was removed and the mixture was left at room temperature. A pale brown suspension was diluted with EA (300 ml) and washed with 10% $NH_4OH$ (1,500 ml). An organic layer was concentrated and applied to $SiO_2$ column chromatography eluting a residue with EA/n-hexane=1/10 to obtain tert-butyl 5-formyl-2,2-dimethyl-1,3-dioxan-5-ylcarbamate (15.0 g, 47.2%) of Chemical Formula 5 as a white solid.

$^1$H NMR (400 MHz, $CDCl_3$): δ 9.64 (s, 1H), 5.56 (s, 1H), 4.07 (d, 2H, J=12.0 Hz), 3.95 (d, 2H, J=12.0 Hz), 1.47 (s, 15H)

0-4. Reaction Formula 4, Synthesis of tert-butyl 5-ethynyl-2,2-dimethyl-1,3-dioxan-5-ylcarbamate

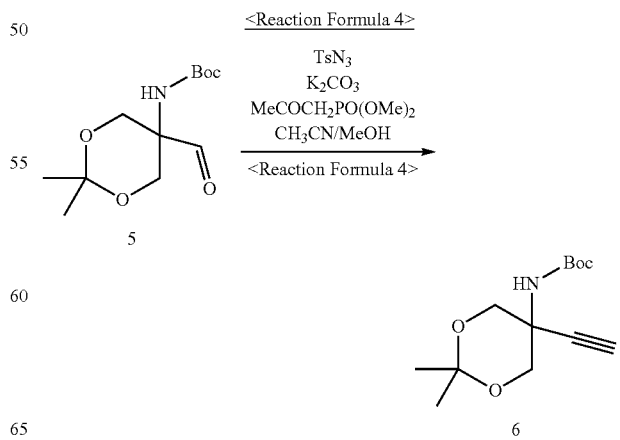

In order to synthesize tert-butyl 5-ethynyl-2,2-dimethyl-1,3-dioxan-5-ylcarbamate of Reaction Formula 4, dimethyl-2-oxopropyl-phosphonate (1.6 g, 1.02 eq) ml) was added in an acetonitrile (50 ml) suspension containing $K_2CO_3$ (3.0 g, 2.25 eq) and p-toluenesulfonylazide (14% solution in toluene, 15.8 ml, 1.05 eq), and the mixture was stirred vigorously at room temperature for 2.5 hours. A solution of tert-butyl 5-formyl-2,2-dimethyl-1,3-dioxan-5-ylcarbamate (2.5 g, 9.64 mmol) of formula 5 contained in methanol (40 ml) was added in a first reaction mixture. After the addition of $K_2CO_3$ (2.7 g, 2.06 eq), the mixture was stirred for 1.5 hours, concentrated under reduced pressure, and the residue was diluted with MC (200 ml) and $H_2O$ (200 ml). An organic layer was washed with $H_2O$ (200 ml), dried on $MgSO_4$ and concentrated under reduced pressure. The organic layer was applied to $SiO_2$ column chromatography while eluting a residual with EA/n-hexane=1/9 to obtain tert-butyl 5-ethynyl-2,2-dimethyl-1,3-dioxan-5-ylcarbamate (2.3 g, 93.4%) of Chemical Formula 6 as a white solid.

$^1$H NMR (400 MHz, $CDCl_3$): δ 5.15 (s, 1H), 4.05-3.95 (m, 4H), 2.43 (s, 1H), 1.48-1.38 (m, 15H)

0-5. Reaction Formula 5, Synthesis of tert-butyl 5-(1-nonanyl-1H-1,2,3-triazol-4-yl)-2,2-dimethyl-1,3-dioxan-5-ylcarbamate

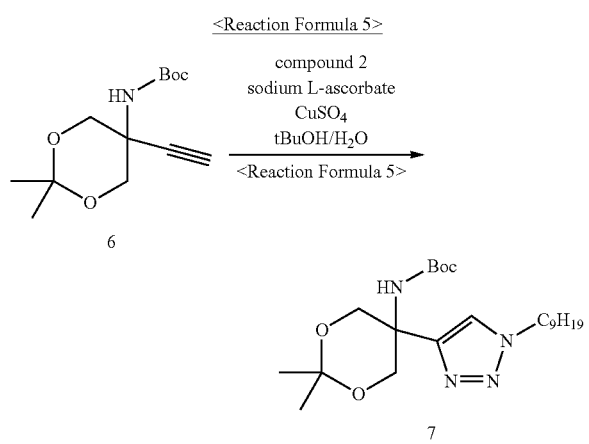

In order to synthesize tert-butyl 5-(1-nonanyl-1H-1,2,3-triazol-4-yl)-2,2-dimethyl-1,3-dioxan-5-ylcarbamate of Chemical Formula 5, $CuSO_4 \cdot 5H_2O$ (2.62 g, 10 mmol) was added in a solution of tert-butyl 5-ethynyl-2,2-dimethyl-1,3-dioxan-5-ylcarbamate (6.7 g, 26 mmol) of Chemical Formula 6, 1-azidononane (4.89 g, 29 mmol) of Reaction Formula 1, sodium L (6.76 g, 34 mmol), t-BuOH (100 ml) and $H_2O$ (214 ml). The two-phase solution was stirred in air at room temperature for 18 hours and diluted with $H_2O$ (300 ml) and MC (100 ml). The organic layer was dried on $MgSO_4$ and concentrated under reduced pressure. The residue was crystallized with n-hexane to obtain tert-butyl 5-(1-nonanyl-1H-1,2,3-triazol-4-yl)-2,2-dimethyl-1,3-dioxan-5-ylcarbamate (9.7 g, 87.8%) of Chemical Formula 7 as a white solid.

$^1$H NMR (600 MHz, $CDCl_3$): δ 7.64 (s, 1H), 5.64 (s, 1H), 4.37 (br, 2H), 4.32 (t, 2H), 4.13 (d, 2H), 1.9 (m, 2H), 1.55 (s, 3H), 1.51 (s, 3H), 1.43 (s, 9H), 1.32-1.25 (m, 12H), 0.88 (t, 3H)

0-6. Reaction Formula 6, Synthesis of 2-amino-2-(1-nonanyl-1H-1,2,3-triazol-4-yl)propane-1,3-diol hydrochloride

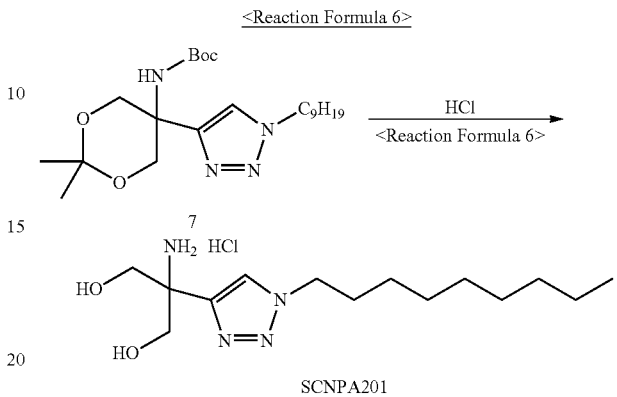

SCNPA201

Figure 1:
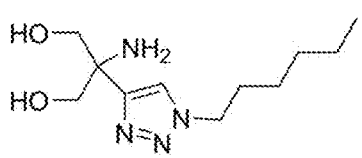
FIG. 1 illustrates Structural Formulas of ASM inhibitory compounds, each substance name and compound are as follows.
Figure 1:
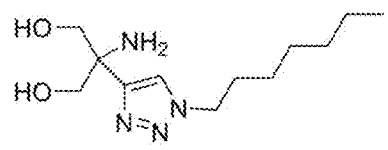
Figure 1:
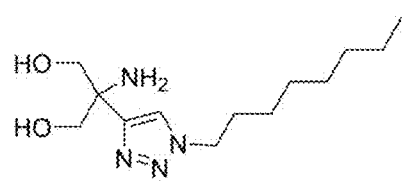
Figure 1:
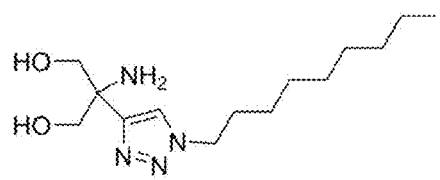
Figure 1:
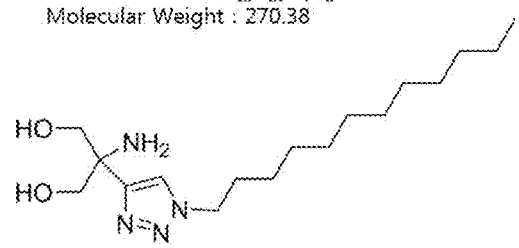

In order to synthesize 2-amino-2-(1-nonanyl-1H-1,2,3-triazol-4-yl)propane-1,3-diol as SCNPA201 of Reaction Formula 6, tert-butyl 5-(1-nonanyl-1H-1,2,3-triazol-4-yl)-2,2-dimethyl-1,3-dioxan-5-ylcarbamate (9.7 g, 20 mmol) of Chemical Formula 7 was mixed with strong HCL (37.9 ml) and ethanol (380 ml), stirred at 40° C. for 6 hours, and then concentrated under reduced pressure. The residue was recrystallized in acetone to obtain 2-amino-2-(1-nonanyl-1H-1,2,3-triazol-4-yl)propane-1,3-diol as a white solid (5 g, 71.2%). The obtained SCNPA201 had Structural Formula as shown in FIG. 1 and had a molecular weight of 284.4.

$^1$H NMR (400 MHz, methanol-$d_4$): δ 8.05 (s, 1H), 4.41 (t, 2H), 3.95 (s, 4H), 1.91 (m, 2H), 1.33-1.21 (m, 12H), 0.91 (t, 3H)

0-7. Synthesis of Substance Name SCNPA501, Compound Name 2-amino-2-(1-hexyl-1H-1,2,3-triazol-4-yl)propane-1,3-diol, Substance name SCNPA401, Compound Name 2-amino-2-(1-heptyl-1H-1,2,3-triazol-4-yl)propane-1,3-diol, Substance Name SCNPA301, Compound Name 2-amino-2-(1-octyl-1H-1,2,3-triazol-4-yl)propane-1,3-diol, and Substance Name SCNPA101, Compound Name 2-amino-2-(1-dodecyl-1H-1,2,3-triazol-4-yl)propane-1,3-diol In Reaction Formula 1 above, 1-bromohexane, 1-bromoheptane, 1-bromooctane, and 1-bromododecane were used as starting materials, and then compounds having Structural Formulas shown in FIG. 1 and molecular weights of SCNPA501=242.32, SCNPA401=257.35, SCNPA301=270.38, and SCNPA101=362.94 were obtained in the same manner as Reaction Formulas 2 to 6 above, respectively.

1. Cell Culture

Human fibroblast lines (normal and PS1) were obtained from Coriell Institute and cultured in a DMEM containing 15% FBS at 37° C. and 5% $CO_2$ and used. Thereafter, the cell lines were treated with 10 μM of each of the synthesized ASM inhibitory compounds and FTY720 (Cayman), and then changes in ASM activity, Ceramide, S1P, and S1PR1 were measured.

2. Mouse

A mouse test was approved by the Kyungpook National University Institutional Animal Care and Use Committee (IACUC). Based on C57BL/6 mice (Charles River, UK), a transgenic mouse line of over-expressing APPswe (hAPP695swe) or PS1 (presenilin-1M146V) was used [hereinafter, APP mouse: mouse over-expressing APPswe, PS1 mouse: mouse over-expressing presenilin-1M146V; GlaxoSmithKline]

In order to confirm the therapeutic effect of ASM inhibition, the synthesized ASM inhibitory compound SCNPA201 (100 mg/kg/day), SCNPA101 (100 mg/kg/day) or FTY720 (1 mg/kg/day) was supplied to 7-month-old mice through water. After 1 month of the supply of water, behavioral analysis was performed, and brain tissues of mice were sampled after behavioral analysis (FIG. 8).

3. Measurement of ASM, Sphk Activity, Ceramide, and S1P

A concentration level of ASM was measured as follows. Specifically, 3 µl of serum, brain tissue, and fibroblast samples of a microliter of the mouse were mixed with an ASM activity buffer and stored at 37° C. 114 µl of ethanol was added and the mixture was centrifuged after terminating a hydrolysis reaction. After 30 µl of a supernatant was transferred to a glass vial, 5 µl of the supernatant was applied to a UPLC system. The ASM concentration level was quantified by comparing aminoacetaldehyde (Bodipy) bound to sphingomyelin and ceramide. To measure a concentration level of Sphk, 3 µl of the fibroblast sample was mixed with a Sphk activity buffer and stored at 37° C. Subsequently, 54 µl of ethanol was added and the mixture was centrifuged after terminating a hydrolysis reaction. After 30 µl of a supernatant was transferred to a glass vial, 5 µl of the supernatant was applied to a UPLC system. Each Sphk concentration level was quantified using a UPLC system by comparing the Sphk concentration level with NBD bound to sphingosine and S1P. For extraction and quantification of Ceramide and S1P, lipids were extracted from the samples by a known method, and the dried lipid extract was resuspended in 25 µl of 0.2% Igepal CA-630 (Sigma-Aldrich), and the concentration levels of Ceramide and S1P were quantified using the UPLC system.

4. ASM Direct Inhibition Test

To obtain ASM IC50 of the synthesized ASM inhibitory compounds, each of the ASM inhibitory compounds was diluted to various concentrations (0 to 200 µM), and then added with ASM and Bodipy-Sphigomyelin as a substrate of ASM and reacted at 37° C. for 10 minutes. After 10 minutes, ethanol was added and the mixture was centrifuged after terminating a hydrolysis reaction. After 30 µl of a supernatant was transferred to a glass vial, 5 µl of the supernatant was applied to a UPLC system. The ASM concentration level was quantified by comparing Bodipy bound to sphingomyelin and ceramide. In order to compare the direct binding energy to ASM with each of the ASM inhibitory compounds, the direct binding energy to ASM was quantified using a Discovery studio program.

5. Immunofluorescence

After immobilization of the cerebrum and hippocampus of a mouse, 0.5% thioflavin S (Sigma-Aldrich), anti-20G10 against Aβ42 (mouse, 1:1000), anti-G30 against Aβ40 (rabbit, 1:1000), and anti-GFAP (rabbit, 1:500, DAKO) were incubated together. The sites were analyzed using a confocal laser scanning microscope or an Olympus BX51 microscope equipped with Fluoview SV1000 imaging software (Olympus FV1000, Japan). Percentages of areas of the stained sites to an area of total tissues were quantified and analyzed using Metamorph software (Molecular Devices).

6. Western Blot

Protein expression of S1PR1 was analyzed using Western blotting. First, antibodies against S1PR1 (abcam) and β-actin (Santa Cruz) were used, and densitometric quantification was performed using ImageJ software (US National Institutes of Health).

7. Real-Time Quantitative PCR

A real-time quantitative PCR method was used to measure the expression levels of inflammatory response-related cytokines (TNF-α, IL-1b, and IL-6). Total RNA was extracted from the brain tissue using an RNeasy Plus mini kit (Qiagen, Korea, Ltd), and cDNA was synthesized from 5 µg of total RNA using a kit from Clontech Co., Ltd. (Mountain View, CA). In addition, by using a Corbett research RG-6000 real-time PCR instrument, real-time quantitative PCR was performed by setting 95° C., 10 min; 95° C., 10 sec; 58° C., 15 sec; 72° C., 20 sec as one cycle and repeating 40 cycles.

Primers used in the real-time quantitative PCR were shown in Table 1.

TABLE 1

| | | |
|---|---|---|
| mTNF-a | 5'-GAT TAT GGC TCA GGG AA-3' (SEQ ID NO: 1) | 5'-GCT CCA GTG AAT TCG GAA AG-3' (SEQ ID NO: 2) |
| mIL-1b | 5'-CCC AAG CAA TAC CCA AAG AA-3' (SEQ ID NO: 3) | 5'-GCT TGT GCT CTG CTT AG-3' (SEQ ID NO: 4) |
| mIL-6 | 5'-CCG GAG AGG AGA CTT CAC AG-3' (SEQ ID NO: 5) | 5'-TTG CCA TTG CAC AAC TCT TT-3' (SEQ ID NO: 6) |
| mGAPDH | 5'-TGA ATA CGG CTA CAG CAA CA-3' (SEQ ID NO: 7) | 5'-AGG CCC CTC CTG TTA TTA TG-3' (SEQ ID NO: 8) |

8. Behavioral Test

In order to confirm a potential effect on learning and memory, a Morris Water Maze (MWM) test was performed. In the MWM, the mouse learned a task 4 times a day for 10 days, a platform was removed on day 11, and aprobe trial was performed. To evaluate activity and anxiety, an open field test and a dark and light test were performed. In the open field test, the mouse was placed in a quadrangular box for 10 minutes and then overall activity and a time spent to move around a wall side and a center were measured. In the dark and light test, the mouse was placed in a quadrangular box consisting of a dark box and a light box for 10 minutes, and a time staying in each box, the number of reciprocating the boxes, and a time to first enter into a light box were measured.

9. Statistical Analysis

For comparison of two groups, a T-test of students was performed, while for comparison of multiple groups, repeated measurement analysis of a Tukey's HSD test and a variance test was performed according to an SAS statistical package (release 9.1; SAS Institute Inc., Cary, NC). *p<0.05, p<0.01, and *p<0.001 were considered to be significant.

Test Results

1. Confirmation of Changes in ASM Activity and Ceramide after Treatment with ASM Inhibitory Compounds in Fibroblasts of Alzheimer's Patient In order to confirm an effect of alleviating Alzheimer's lesions by ASM inhibition in vitro, ASM inhibitory compounds SCNPA501, SCNPA401, SCNPA301, SCNPA 201, and FTY720 were treated at concentrations of 10 µM in fibroblasts derived from Alzheimer's patients, and then changes in ASM activity were first measured.

The FTY720 was not initially developed as an ASM inhibitor, but was proved to have an ASM inhibitory effect by various research results, and then was used as a positive control for comparing the effects in the present invention (Biochem Biophys Res Commun. 2011 Jan. 7; 404(1):321-323).

As a result of the test, the ASM activity was significantly increased in PS1 fibroblasts as compared to normal human-derived fibroblasts, but was significantly reduced by treatment with the ASM inhibitory compounds SCNPA501, SCNPA201, SCNPA301, and SCNPA 201 (FIG. 2a), and Ceramide, a product produced by the ASM activity, was also significantly reduced by treatment with the ASM inhibitory compounds (FIG. 2b).

2. Confirmation of Effect of Directly Inhibiting ASM Activity by ASM Inhibitory Compounds To confirm whether the ASM inhibitory compounds of the present invention may directly inhibit the ASM activity, as a result of confirming the concentration capable of inhibiting the ASM activity by 50% by reacting an ASM enzyme and sphigomyelin as a substrate of ASM enzyme with the ASM inhibitory compounds at various concentrations, it was confirmed that all compounds can inhibit the ASM activity at low concentrations (SCNPA501=1.86 µM, SCNPA401=1.82 µM, SCNPA301=1.75 µM, SCNPA 201=1.14 µM) (FIG. 3a).

Further, in order to confirm whether the ASM inhibitory compounds directly bind to the ASM to inhibit the activity, Docking simulation was performed. In order to confirm whether the ASM inhibitory compounds bind to ASM active sites, the binding sites of the ASM and Phosphocholine of Sphingomyelin as a substrate were compared. As a result, it was confirmed that neighboring amino acids (D206, D278, H319, N318, etc.) involved in the binding of the ASM and the phosphocholine of Sphingomyelin were mostly similar to amino acids involved in the binding of the ASM activity inhibitory compounds of the present invention and the ASM (FIG. 3b).

In other words, it can be seen that the ASM inhibitory compounds of the present invention directly bind to the ASM active sites, that is, the sites to which the phosphocholine of Sphingomyelin as a substrate binds.

Meanwhile, according to conventional studies, it has been reported that the expression level of an ASM protein was increased in the brain of Alzheimer's patients (Neurobiology of Aging 31 (2010) 398-408), and the expression level of the ASM protein was also increased even in the brain of patients with multiple sclerosis, one of the neurodegenerative diseases (SCIENTIFIC REPORT (2018) 8:3071).

However, referring to the results of FIG. 3b, since the ASM inhibitory compounds according to the present invention exhibit activity of directly binding to the ASM protein, if a diagnostic substance such as a fluorescent substance is labeled, the expression level of the ASM protein may be quantified from a subject or a biological sample obtained from the subject.

Therefore, it can be determined that the ASM inhibitory compounds according to the present invention may be used for diagnosis or prognosis of neurodegenerative diseases by quantifying the expression level of the ASM protein from a subject or a biological sample obtained from the subject.

3. Confirmation of Changes in S1P and S1PR1 by ASM Inhibitory Compounds

In the case of FTY720, it has been known that the FTY720 reacted with a Sphk enzyme instead of Sphingosine to inhibit the activity of Sphk and was converted into phosphorylated phospho-FTY720 to reduce the expression of S1P which is a sphingosine product. In addition, it has been known that the phosphorylated phospho-FTY720 was bound to a S1P1 receptor (S1PR1) to reduce the expression of the S1P1 receptor.

In order to confirm whether the ASM inhibitory compounds of the present invention exhibit such an effect, after the ASM inhibitory compounds SCNPA501, SCNPA401, SCNPA301, SCNPA 201, and FTY720 were treated in normal fibroblasts or fibroblasts derived from Alzheimer's patients at concentrations of 10 µM, changes in Sphk activity, S1P and S1PR1 were first measured.

As a result, it was confirmed that the FTY720 reduced the Sphk activity and the expression of S1P and S1PR1, whereas the ASM inhibitory compounds did not exhibit these effects (FIGS. 4a and 4b). As these results, it was confirmed that the ASM inhibitory compounds of the present invention may specifically inhibit only the activity of ASM, and show a different pharmacological mechanism from the FTY720.

4. Pharmacokinetic Evaluation of ASM Inhibitory Compounds

In order to compare the pharmacokinetic properties of the ASM inhibitory compounds, pharmacokinetic tests of SCNPA501, SCNPA201 and SCNPA101 were compared and analyzed.

The SCNPA101 was a compound previously confirmed to have ASM inhibitory activity by the present inventors, and was used in a test for comparison with the ASM inhibitory compounds SCNPA201 and SCNPA501 according to the present invention.

After SCNPA501, SCNPA201 and SCNPA101 were injected into normal mice through oral (10 mg/kg) or tail vein (1 mg/kg), respectively, bloods were collected on 5 minutes, 15 minutes, 30 minutes, 1 hour, 2 hours, 4 hours, 8 hours and 24 hours, respectively, and the blood concentration of each compound was measured (FIG. 5a). As a result of analyzing pharmacokinetic parameters, it was found that SCNPA501 (72.26%) and SCNPA201 (50.33%) had higher bioavailability (BA) percentages than SCNPA101 (19.64%) and thus was more effective as an oral administration preparation (FIG. 5b).

5. Confirmation of Brain Distribution of ASM Inhibitory Compounds

For the application of the ASM inhibitory compounds of the present invention to degenerative brain diseases, it is important that the ASM inhibitory compounds were injected and then well distributed in the brain with the increased ASM. To confirm this, SCNPA501, SCNPA201 and SCNPA101 were administered orally (10 mg/kg), and then the brain was extracted for each time period to measure the concentrations, and after 24 hours, the brain, liver, kidney, and heart were extracted to measure the concentrations. As a result, it was confirmed that the concentration of SCNPA201 in the brain was remarkably high (FIG. 6a).

On the other hand, as a result of confirming the pharmacokinetic parameters in the brain, brain distribution values were confirmed as SCNPA501 (1.41), SCNPA201 (3.64), and SCNPA101 (3.61) (FIG. 6b).

From the above results, it can be seen that in terms of pharmacokinetics, SCNPA201 exhibits a more ideal brain distribution than SNCPA101, and thus may be more usefully used in the development of therapeutic agents for brain diseases such as neurodegenerative diseases.

6. Confirmation of Liver Microsome Stability of ASM Inhibitory Compounds

In order to confirm the metabolic stability of the ASM inhibitory compounds, a remaining amount of each compound was checked after 30 minutes after treatment with SCNPA501, SCNPA201 or SCNPA101 in human or mouse liver microsomes.

As a result, it was confirmed that the stability was higher in the order of SCNPA501 (98.21%), SCNPA201 (95.66%), and SCNPA101 (86.36%) in mouse liver microsomes, and the same trend was also shown in human liver microsomes. In particular, in human liver microsomes, it was confirmed that the stability of SCNPA101 was very low as 7.8% as compared with SCNPA201 and SCNPA501 (FIGS. 7a and 7b).

As these results, it could be seen that SCNPA101 has very low metabolic stability in human liver microsomes, whereas the ASM inhibitory compounds SCNPA501 and SCNPA201 of the present invention had high metabolic stability.

In particular, in the case of SCNPA101, the metabolic stability by mouse liver microsomes was not significantly poor, but the metabolic stability by human liver microsomes was very poor, and thus, test results using mice and clinical results when applied actually to humans may be completely different from each other. It was confirmed that these metabolic characteristics may be shown as a big limitation in the development of oral administration agents that need undergo a liver first pass effect. That is, in the test results of the "pharmacokinetic evaluation", the mouse bioavailability of SCNPA101 is shown as 19.64%, but when applied to humans, it may be expected that the SCNPA101 is significantly metabolized by the liver after oral administration, and the bioavailability of SCNPA101 is lower than that of the mouse.

On the contrary, the ASM inhibitory compounds in the present invention are considered to have superior metabolic stability by human liver microsomes compared to SCNPA101, and thus, it may be expected that a pharmacological effect and efficacy persistence when administered actually to persons are remarkably superior to SCNPA101.

7. Confirmation of Changes in ASM Activity in Alzheimer's Animal Model Administered with ASM Inhibitory Compounds In order to verify an effect of alleviating Alzheimer's lesions by inhibiting ASM activity in vivo, a therapeutic effect of SCNPA201, which was an ASM inhibitory compound, was compared with those of SCNPA101 and FTY720 using an Alzheimer's test animal model (AD: APP/PS1 mouse). In order to compare the Alzheimer's therapeutic effect, SCNPA201 (100 mg/kg/day), SCNPA101 (100 mg/kg/day) or FTY720 (1 mg/kg/day) was supplied to a 7-month-old Alzheimer's animal model through water (FIG. 8).

First, in order to check whether the ASM activity was inhibited, the plasma and brain tissue of each Alzheimer's animal model were extracted to confirm the ASM activity.

As a result, it was confirmed that the ASM concentration levels in the plasma (FIG. 9a) and the brain tissue (FIG. 9b) of the Alzheimer's animal model administered with SCNPA201 were lowest.

8. Confirmation of Amyloid-β Deposition in Alzheimer's Animal Model Administered with ASM Inhibitory Compounds In order to confirm whether the inhibition of ASM activity by administration of the ASM inhibitory compounds has an effect on Alzheimer's lesions, first, the medulla and hippocampus regions of the mouse were stained with Thioflavin S (ThioS) according to a known method to confirm protofibril amyloid-β deposition. In addition, immunofluorescence staining of Aβ40 and Aβ42 was performed to confirm the amyloid-β deposition.

As a result of the test, it was confirmed that protofibril Aβ deposition (FIG. 10) and Aβ40 and Aβ42 deposition were lowest in an APP/PS1 mouse administered with SCNPA201 compared to an APP/PS1 mouse (FIGS. 11a and 11b). This effect showed a better effect than an APP/PS1 mouse injected with SCNPA101 or FTY720.

9. Confirmation of Improved Memory in Alzheimer's Animal Model Administered with ASM Inhibitory Compounds In order to confirm whether ASM inhibition by administration of the ASM inhibitory compounds shows a potential effect on memory in an Alzheimer's animal model, a Morris Water Maze (MWM) test was performed.

As illustrated in FIGS. 12a to 12c, it was confirmed that the APP/PS1 mouse showed a serious impairment in the formation of cognition, but in the case of a mouse administered with SCNPA201, an effect of improving cognition was more remarkable as compared to SCNPA101 or FTY720.

In addition, an open field test and a dark & light test were conducted to confirm an effect of the ASM inhibitory compounds on activity and anxiety.

As illustrated in FIGS. 13a and 13b, it was confirmed that the activity and anxiety were improved in an APP/PS1 mouse administered with SCNPA201 or SCNPA101 compared to an APP/PS1 mouse. In particular, it was confirmed that SCNPA201 has a more remarkable effect of improving activity and anxiety than SCNPA101. On the other hand, it was confirmed that this effect was not shown in an APP/PS1 mouse administered with FTY720.

10. Confirmation of Changes in Neuroinflammation in Alzheimer's Animal Model Administered with ASM Inhibitory Compounds In an Alzheimer's animal model, in order to confirm an effect of ASM inhibition by injection of the ASM inhibitory compounds on changes in neuroinflammation, changes in astrocytes in the brain were observed. Compared with the APP/PS1 mouse, it was confirmed that the activity of astrocytes was significantly decreased in the APP/PS1 mouse administered with SCNPA201 or SCNPA101 (FIG. 14a). In particular, the activity of astrocytes decreased largest in the brain of the APP/PS1 mouse administered with SCNPA201 as compared with in the APP/PS1 mouse administered with SCNPA101. On the other hand, it was confirmed that this effect was not shown in an APP/PS1 mouse administered with FTY720.

In addition, in the APP/PS1 mouse, the gene expression of inflammatory cytokines TNF-a, IL-1b, and IL-6 was significantly increased compared to a wild mouse, but in the APP/PS1 mouse administered with SCNPA201 or SCNPA101, it was confirmed that the expression of the inflammatory cytokines was restored to a normal level (FIG. 14b). In particular, it was confirmed that the expression of these inflammatory cytokines was significantly reduced in the brain of the APP/PS1 mouse administered with SCNPA201 as compared with the APP/PS1 mouse administered with SCNPA101, and this effect was not shown in the APP/PS1 mouse administered with FTY720.

Summarizing the above results, it can be seen that the ASM inhibitory compounds SCNPA501, SCNPA401, SCNPA301, and SCNPA201 can significantly inhibit the activity of ASM in fibroblasts of Alzheimer's patients, and also bind to the ASM active sites to directly inhibit the activity of ASM. On the other hand, it can be seen that since the ASM inhibitory compounds did not exhibit the effect of inhibiting the Sphk activity, S1P, and S1PR1, the ASM inhibitory compounds were direct inhibitors capable of specifically inhibiting ASM. In addition, it was confirmed once again that the ASM inhibitory compounds of the present invention can be directly bound to the ASM active sites to be used for diagnosis of brain diseases in which the ASM is increased.

In addition, according to the pharmacokinetic test and brain distribution results, it can be seen that the ASM inhibitory compounds of the present invention show a better effect than the existing ASM activity inhibitor SCNPA101 developed by the present inventors. Particularly, it can be seen that in human liver microsomes, the metabolic stability of SCNPA101 is very low, whereas the ASM inhibitory compounds of the present invention have high metabolic stability to have a significantly excellent possibility to be developed as a drug formulation.

Likewise, in a therapeutic effect in the Alzheimer's animal model, the ASM inhibitory compounds of the present invention show a better therapeutic effect in inhibiting ASM activity in the brain, reducing Aβ plaques, improving memory and depression, alleviating neuroinflammation, etc. than SCNPA101 or FTY720. Therefore, it can be seen that that the ASM inhibitory compounds of the present invention can be used as an agent for preventing or treating neurodegenerative diseases such as Alzheimer's disease and depression.

INDUSTRIAL APPLICABILITY

An ASM inhibitory compound of Chemical Formula 1 of the present invention has an excellent effect of inhibiting ASM by directly binding to an ASM protein, has therapeutic effects such as reducing Aβ plaques, improving memory and anxiety, and alleviating neuroinflammation in an Alzheimer's brain environment, has a very high distribution in the brain, and has very excellent metabolic stability by liver microsomes and thus, may be very usefully used in developing an agent for preventing or treating neurodegenerative diseases including Alzheimer's disease, and a composition for diagnosing neurodegenerative diseases. In addition, as previously reported that inhibition of ASM is effective in relieving depression, a novel compound of inhibiting ASM of Chemical Formula 1 of the present invention may be usefully used as an agent for preventing or treating neurological diseases including depression. Therefore, the present invention has very excellent industrial applicability.

What is claimed is:

1. A compound of Chemical Formula 1 below or a salt thereof:

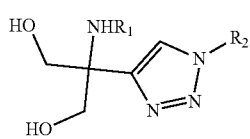

[Chemical Formula 1]

wherein, $R_1$ is hydrogen, and $R_2$ is alkyl of 6 to 9 carbon atoms.

2. A composition comprising a compound of Chemical Formula 1 below or a pharmaceutically acceptable salt thereof:

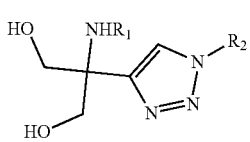

[Chemical Formula 1]

wherein, $R_1$ is hydrogen, and $R_2$ is alkyl of 6 to 9 carbon atoms.

3. The composition of claim 2, wherein the compound of Chemical Formula 1 is 2-amino-2-(1-hexyl-1H-1,2,3-triazol-4-yl)propane-1,3-diol, 2-amino-2-(1-heptyl-1H-1,2,3-triazol-4-yl)propane-1,3-diol, 2-amino-2-(1-octyl-1H-1,2,3-triazol-4-yl)propane-1,3-diol, or 2-amino-2-(1-nonyl-1H-1,2,3-triazol-4-yl)propane-1,3-diol.

4. The composition of claim 2, wherein the composition is orally administered.

5. The composition of claim 2, wherein the composition is a pharmaceutical composition or a food composition.

6. A composition comprising a compound of Chemical Formula 1 below or a pharmaceutically acceptable salt thereof and a diagnostic agent or detection agent:

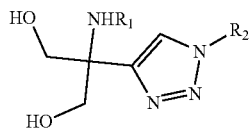

wherein R₁ is hydrogen, and R₂ is alkyl of 6 to 9 carbon atoms.

7. A method for treating a neurodegenerative disease or depression comprising administering an effective amount of a composition containing a compound of Chemical Formula 1 below or a pharmaceutically acceptable salt thereof to a subject in need thereof:

[Chemical Formula 1]

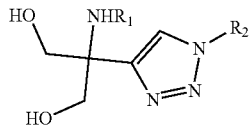

wherein, R₁ is hydrogen and R₂ is alkyl of 6 to 9 carbon atoms.

8. The method of claim 7, wherein the compound of Chemical Formula 1 exhibits an effect of inhibiting acid sphingomyelinase (ASM) activity.

9. The method of claim 7, wherein the neurodegenerative disease is at least one selected from the group consisting of Alzheimer's disease, Parkinson's disease, progressive supranuclear palsy, multiple system atrophy, olivopontocerebellar atrophy (OPCA), Shire-Dragger syndrome, striatumnigral degeneration, Huntington's disease, amyotrophic lateral sclerosis (ALS), essential tremor, corticobasal degeneration, diffuse Lewy body disease, Parkin's-ALS-dementia complex, pick disease, cerebral ischemia, and cerebral infarction.

10. A method for diagnosing a neurodegenerative disease or depression comprising administering an effective amount of a composition containing a compound of Chemical Formula 1 below or a pharmaceutically acceptable salt thereof to which a diagnostic agent or detection agent is bound to a subject suspected of a neurodegenerative diseases or depression:

[Chemical Formula 1]

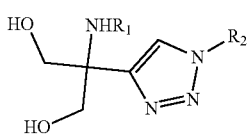

wherein, R₁ is hydrogen, and R₂ is alkyl of 6 to 9 carbon atoms.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: mTNF-a forward

<400> SEQUENCE: 1
gattatggct cagggtccaa                                             20

<210> SEQ ID NO 2
<211> LENGTH: 20
<212> TYPE: DNA
<213> ORGANISM: Artificial Sequence
<220> FEATURE:
<223> OTHER INFORMATION: mTNF-a reverse

<400> SEQUENCE: 2
gctccagtga attcggaaag                                             20

<210> SEQ ID NO 3
<211> LENGTH: 20
<212> TYPE: DNA
<213> ORGANISM: Artificial Sequence
<220> FEATURE:
<223> OTHER INFORMATION: mIL-1b forward

<400> SEQUENCE: 3
cccaagcaat acccaaagaa                                             20

<210> SEQ ID NO 4
<211> LENGTH: 20
```

```
<212> TYPE: DNA
<213> ORGANISM: Artificial Sequence
<220> FEATURE:
<223> OTHER INFORMATION: mIL-1b reverse

<400> SEQUENCE: 4
gcttgtgctc tgcttgtgag                                               20

<210> SEQ ID NO 5
<211> LENGTH: 20
<212> TYPE: DNA
<213> ORGANISM: Artificial Sequence
<220> FEATURE:
<223> OTHER INFORMATION: mIL-6 forward

<400> SEQUENCE: 5
ccggagagga gacttcacag                                               20

<210> SEQ ID NO 6
<211> LENGTH: 20
<212> TYPE: DNA
<213> ORGANISM: Artificial Sequence
<220> FEATURE:
<223> OTHER INFORMATION: mIL-6 reverse

<400> SEQUENCE: 6
ttgccattgc acaactcttt                                               20

<210> SEQ ID NO 7
<211> LENGTH: 20
<212> TYPE: DNA
<213> ORGANISM: Artificial Sequence
<220> FEATURE:
<223> OTHER INFORMATION: mGAPDH forward

<400> SEQUENCE: 7
tgaatacggc tacagcaaca                                               20

<210> SEQ ID NO 8
<211> LENGTH: 20
<212> TYPE: DNA
<213> ORGANISM: Artificial Sequence
<220> FEATURE:
<223> OTHER INFORMATION: mGAPDH reverse

<400> SEQUENCE: 8
aggcccctcc tgttattatg                                               20
```